US009539385B2

(12) United States Patent
Mathys

(10) Patent No.: US 9,539,385 B2
(45) Date of Patent: Jan. 10, 2017

(54) INFUSION PUMP DEVICE WITH VENTING FEATURE

(71) Applicant: TecPharma Licensing AG, Burgdorf (CH)

(72) Inventor: René Mathys, Aarau (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 14/506,197

(22) Filed: Oct. 3, 2014

(65) Prior Publication Data
US 2015/0080842 A1 Mar. 19, 2015

Related U.S. Application Data

(63) Continuation of application No. PCT/EP2013/056936, filed on Apr. 2, 2013.

(30) Foreign Application Priority Data

Apr. 5, 2012 (CH) .......................................... 480/12
Dec. 18, 2012 (CH) ....................................... 2848/12

(51) Int. Cl.
A61M 5/14 (2006.01)
A61M 5/142 (2006.01)
(Continued)

(52) U.S. Cl.
CPC ....... *A61M 5/14244* (2013.01); *A61M 5/1452* (2013.01); *A61M 5/31* (2013.01);
(Continued)

(58) Field of Classification Search
CPC .. A61M 5/1452; A61M 5/1413; A61M 5/142; A61M 2005/14268; A61M 5/14244; A61M 5/24; B65D 51/16; F04B 43/082; F04B 43/1223
See application file for complete search history.

(56) References Cited

U.S. PATENT DOCUMENTS 3,756,233 A * 9/1973 Goldowsky .................. 604/254
3,963,024 A * 6/1976 Goldowsky .................. 604/254
(Continued)

FOREIGN PATENT DOCUMENTS

EP 0985419 3/2000
EP 1426662 6/2004
(Continued)

*Primary Examiner* — Scott Medway
(74) *Attorney, Agent, or Firm* — Dorsey & Whitney LLP; Stuart R. Hemphill, Esq.

(57) ABSTRACT

An infusion device for infusion of a fluid from a reservoir into a body, the infusion device being connectable to an infusion set adaptor at a connecting site, the infusion device comprising: a drive mechanism to operatively couple with at least a portion of the reservoir; a housing being sized to contain at least a portion of the reservoir, wherein the drive mechanism is at least partially or fully contained within the housing; a sealing device that permits the passage of air into and out of the housing or a housing compartment and inhibits the passage of liquids into the housing or a housing compartment through the sealing device; wherein the sealing device is arranged at the drive mechanism or at a location between a part of the drive mechanism and the connecting site of the infusion set adaptor or at the connecting site of the infusion set adaptor.

18 Claims, 12 Drawing Sheets

(51) Int. Cl.
  *A61M 5/145*   (2006.01)
  *A61M 5/31*   (2006.01)
(52) U.S. Cl.
  CPC ............ *A61M 2005/14264* (2013.01); *A61M 2005/14506* (2013.01); *A61M 2005/3123* (2013.01); *A61M 2205/12* (2013.01); *A61M 2205/332* (2013.01); *A61M 2205/7536* (2013.01); *A61M 2207/00* (2013.01)

(56) References Cited

U.S. PATENT DOCUMENTS

| | | | | |
|---|---|---|---|---|
| 4,203,463 | A | * | 5/1980 | Ponlot et al. ................. 137/403 |
| 4,325,368 | A | * | 4/1982 | Kaemmerer .................... 604/80 |
| 5,509,898 | A | * | 4/1996 | Isono et al. ..................... 604/87 |
| 5,993,423 | A | | 11/1999 | Choi |
| 6,248,093 | B1 | | 6/2001 | Moberg |
| 7,597,682 | B2 | | 10/2009 | Moberg |
| 8,491,529 | B2 | * | 7/2013 | Yodfat et al. ................. 604/131 |
| 2004/0092873 | A1 | * | 5/2004 | Moberg ......................... 604/131 |
| 2005/0197626 | A1 | | 9/2005 | Moberg et al. |
| 2005/0245882 | A1 | * | 11/2005 | Elkins et al. ................. 604/239 |
| 2008/0312595 | A1 | * | 12/2008 | Elmouelhi et al. ........... 604/151 |

FOREIGN PATENT DOCUMENTS

| | | |
|---|---|---|
| WO | WO 2004/091688 | 10/2004 |
| WO | WO 2004091688 A2 * | 10/2004 |
| WO | WO 2010/026580 | 3/2010 |

* cited by examiner

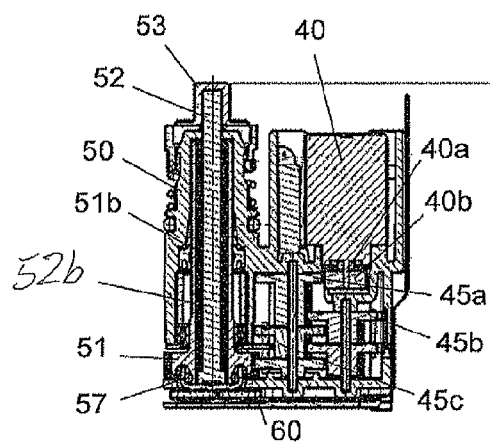
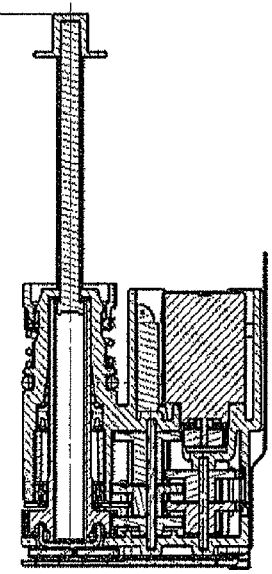
Figure 3c
Figure 3f
Figure 3b
Figure 3e
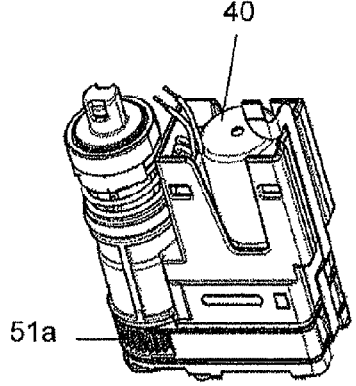
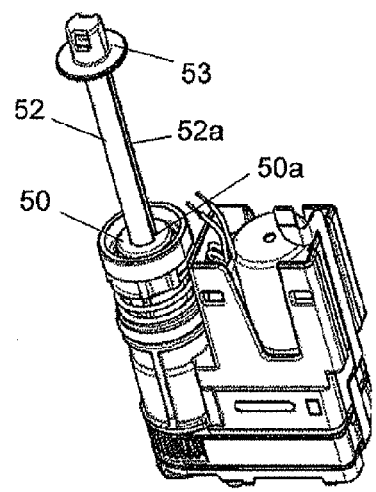
Figure 3a
Figure 3d

INFUSION PUMP DEVICE WITH VENTING FEATURE

CROSS-REFERENCE TO RELATED APPLICATIONS

This application is a Continuation of International Patent Application No. PCT/EP2013/056936 filed Apr. 2, 2013, which claims priority to Swiss Patent Application No. 00480/12 filed Apr. 5, 2012 and Swiss Patent Application No. 02848/12 filed Dec. 18, 2012, the entire contents of each are incorporated herein by reference.

BACKGROUND

The present invention relates to a device or portable administering apparatus for administering a fluid product, in particular medical substances or a drug in liquid form. In particular the invention relates to a portable infusion pump and/or infusion systems such as insulin pumps. Such a device is referred to in the following as an administering device.

In the case of various diseases, it can be necessary to administer a patient over a longer period of time with a drug which is provided in liquid form, for example an insulin preparation or a haemodiluting drug such as heparin. Compact portable infusion apparatuses are known for this purpose and are continuously carried around close to the body by the patient. In most cases, a carpule is provided as the drug container in such infusion apparatus, i.e. a plastic or glass container comprising a plug which can be moved within it. The carpule (often also referred to as a carpoule, an ampoule or a reservoir) is connected to an infusion set, the cannula of which feeds into the body tissue of the patient. The plug or stopper is advanced in the carpule by a suitable drive, for example, a spring drive or an electric motor, and the drug is thus expelled from the carpule. As soon as the carpule is empty, it is removed from the infusion apparatus and replaced with a new carpule.

In many portable infusion apparatuses, the plug is advanced in the carpule via a threaded rod which acts as a piston rod for the plug. A nut which is mounted such that it is rotatable but fixed against shifting runs on the threaded rod and is driven by an electric motor. Rotating the nut advances the threaded rod, wherein the electric motor is, in general, arranged next to the carpule in order to limit the length of the infusion apparatus and to simplify exchanging the carpule.

U.S. Pat. No. 6,248,093 B1 discloses an infusion apparatus in which the drive motor and a gear system are arranged coaxially with the drug reservoir. The plug of the drug reservoir is advanced by a sleeve-like advancing element which is connected via an inner thread to a drive screw, which is driven by the motor, and thus linearly advanced. In its initial position, the advancing element at least partially surrounds the gear system of the motor, wherein the advancing element is a part of the base unit, while the plug is part of the exchangeable drug reservoir. The advancing element and the plug are therefore embodied such that they can be separated from each other. In order to ensure that the drug is not undesirably expelled by fluctuations in the ambient pressure, the advancing element and the plug are connected such that the connection can also absorb tensile forces while the infusion apparatus is in operation. In this way, the plug necessarily follows the movement of the advancing element and cannot be advanced, by pressure fluctuations, further than is predetermined by the position of the advancing element. When the drug reservoir is exchanged, the plug and the advancing element are separated from each other by a rotational movement. The advancing element is then moved back into its initial position by the motor. On the one hand, this arrangement requires a relatively complicated connection between the plug and the advancing element; particular steps also have to be taken in case a drug reservoir which is not completely filled is used.

An infusion apparatus is known from EP 0 985 419 A1 in which the drive motor and a drug reservoir are arranged antiparallel with respect to each other, wherein a gear system transmits the drive movement from the motor to an advancing element which is arranged coaxially with respect to the reservoir and in turn moves the plug provided in the drug reservoir, thus displacing the drug from the reservoir. A so-called infusion set adaptor is attached to the exit of the drug reservoir and channels the drug into an infusion set. In order to ensure that the drug is not undesirably expelled by fluctuations in the ambient pressure, a threshold value valve is arranged in the infusion set adaptor and requires a particular drive pressure in order to enable liquid to be transported through the infusion set adaptor at all. As compared to the variant described above, in which the plug is retained by the advancing element, the threshold value valve has the advantage that standard carpules for the infusion apparatus can be used; in particular, specially shaped plugs are not required. It is, however, known that when the threshold value valve is a membrane valve, an inaccurate positioning of the valve membrane can potentially lead to malfunctions and in particular valve leakage, and that accurately positioning the membrane presents a production-related challenge.

U.S. Pat. No. 5,993,423 describes a portable automatic syringe device and an injection needle unit thereof.

U.S. Pat. No. 7,597,682 B2 describes an external infusion device for infusion of a fluid into a body from a reservoir including a drive system, a housing, an electronic control circuitry and at least one vent port. The vent port in the housing permits the passage of air into and out of the housing and inhibits the passage of liquids into the housing.

A user of an administering device may travel through various elevations, which might occur when hiking in the mountains or travelling in an airplane, so that differential pressures can arise between the interior of the air tight or water-resistant pump housing and the outside or atmosphere. Once the pressure in the housing exceeds the external atmospheric pressure, resulting forces could cause the reservoir plug or reservoir piston to be driven inwards, thus delivering unwanted medication. Problems with the correct functioning of the administering device may also occur in case the outside atmospheric pressure exceeds the inside pressure of the housing.

It is desirable to have an administering device which guarantees safe operation among various atmospheric pressures.

SUMMARY

It is an object of an embodiment of the present invention to provide an administering device or infusion device with a vented housing.

It is a further object of the invention to provide a device for administering a fluid product, comprising an infusion set and an administering apparatus, which offers increased reliability and improved safety and which can be operated with standard-dimension carpules.

These objects are solved by the present disclosure, which provides infusion devices for administering a fluid product that inter alia includes an infusion set and an administering apparatus.

Such a device comprises an actual administering apparatus, in particular an infusion pump, and an infusion set which establishes a liquid connection between the administering apparatus and an injection needle, wherein the administering needle is injected into the tissue of the person using the device, in order to administer a fluid product, for example, a liquid drug.

The design of the administering apparatus may include similarities to known mobile infusion pumps, such as those currently sold by manufacturers such as Roche or Medtronic, where the administering apparatus includes: a housing; a container for the product, which is at least partially accommodated by the housing; a conveying means for conveying the product from the container; and a drive device. The infusion set generally includes at least one single-part or multi-part adaptor which establishes a liquid connection between the product container and the infusion set and which can be detachably fastened to the administering apparatus.

The drive device comprises a drive motor and a controller. In a particular example, the drive device also comprises a spindle drive which acts on the conveying means. In another example, a gear system is arranged between the drive motor and the spindle drive and gears up or gears down the movement of the motor. In one example, the container filled with product can be a pre-filled ampoule, in particular, a so-called carpule. Alternatively, the container can also be a reservoir which is to be filled by the person using the device. Common to all the examples of the containers is that they can be inserted into a receiving compartment, formed or defined by the housing, and exchanged. The product may be a medical and/or cosmetic active agent solution, emulsion or suspension. The conveying means may be a stopper, a piston or a plug. The device is generally worn continuously by the person using it, either on their body or on or in their clothing.

In one example, the administering apparatus comprises at least one means for determining a malfunction of the device. This malfunction can be due to an occlusion or a leakage on the product's path from the container to an outlet of the injection needle. Another example of a malfunction can be due to the drive device, for example, a faulty or disrupted drive motor or a faulty controller and/or regulator for a drive motor.

In one example, the administering apparatus comprises an input means and a display means, wherein the input means and display means can be at least partially combined, for instance, as a touch display, wherein the combination of a touch display and an individual key (e.g., a function key) which is distinct from the touch display may be preferred. Other input means can be provided, such as for example a speech input. In principle, the input means and display means enable the person using the device to personally influence how product is administered. In one advantageous improvement, the key is arranged in the housing of the administering apparatus, forming a seal, such that water cannot enter the interior of the administering apparatus or the interior of the key.

In one example, the adaptor of the infusion set comprises a housing, wherein an open cylinder is arranged on one side of the housing and can be introduced into an opening of the receiving compartment of the administering apparatus. For the purpose of fastening the cylinder in the receiving compartment, elements are arranged on the outer surface of the cylinder shell and can be engaged with matching counter-elements on the inner surface of the receiving compartment, wherein they can be engaged by inserting the cylinder along the longitudinal axis of the receiving compartment or alternatively via a screw connection or a bayonet lock. In the interior of the cylinder, a so-called connecting needle is arranged coaxially with respect to the axis of the cylinder. When an adaptor is inserted into the administering apparatus, the hollow connecting needle pierces a wall of the product container, in particular a septum, and establishes a liquid connection between the container and the infusion set. An opening is arranged on another side of the adaptor housing, and the catheter of the infusion set can be detachably or non-detachably arranged in said opening, where a liquid path is arranged in the housing such that a liquid connection between the connecting needle and the catheter is established. In one potentially advantageous embodiment of this example, a valve is arranged in the liquid path of the housing. This valve may prevent any undesirable leakage from the product container, to such an extent that the person using the device cannot receive any incorrect dosage which would be hazardous to them. This may be important in particular when there is a difference in pressure between the administering apparatus and the injection needle. The administering apparatus can for example be arranged higher than the injection needle. The force and/or pressure of the column of liquid which is then present can thus cause the product container to be emptied if there is not a sufficiently large resistance or counter-pressure inside the product container. Since the quality of typical product containers (e.g., carpules) is subject to fluctuations in production, and the piston or plug is arranged such that it can be shifted in the carpule exhibits a fluctuating plug friction against the carpule wall, a means which enables product to be administered only once a minimum drive force is exerted by the drive device becomes necessary. The valve arranged in the adaptor is essentially closed when the administering apparatus is in its resting state. Only once the drive device is activated and a sufficiently high and defined pressure is acting on the valve, does the valve open and enable larger amounts of product to flow through it. In one example, the valve can be a membrane valve, wherein the valve membrane is positioned, centered, on the valve seating. By centering the valve is it possible to ensure that the valve only opens at a defined pressure. If the centering is off, then the periphery of the valve membrane may touch an inner wall of the valve. Consequently, the periphery of the valve membrane will rub against the wall of the valve. When the drive device is activated, this can cause the membrane for opening the valve to open due to the operation-related pressure, i.e. to move at its periphery, but to no longer return to its initial position when the drive device is deactivated, due to the friction between the periphery and the wall, thus leaving the valve leaky. In order to obviate this problem, implementations of the valve may include centering aids which simplify centering the valve membrane in the valve. Nub-like structures on the periphery of the valve membrane or the part of the valve wall facing the periphery of the valve membrane can for example serve to center the valve. In the resting state, these structures establish a punctate contact between the membrane and the wall. When the valve is opened by deforming the membrane, the contact is lost due to the deformation, such that factional forces cannot prevent the membrane from returning to its initial position. At least three such structures may be necessary in order to correctly center the typically circular membrane. Because of how the valve membrane and valve space are dimensioned, two of the at least three structures typically touch the wall or the periphery of the membrane, respectively, once the membrane has been inserted, since the inner diameter of the interior space of the valve is chosen to be larger than the outer diameter of the valve membrane.

In one example, the adaptor has an arcuate shape, i.e. the connecting needle is arranged coaxially with respect to the receiving compartment when the adaptor is inserted and the opening for the catheter projects about 90° from the axis of the receiving compartment. In one arrangement of the opening, the catheter is guided out of the opening obliquely relative to the lateral edges of the administering apparatus. This has ergonomic advantages for the person using the device.

In one example, the adaptor can only be placed onto the administering apparatus in a particular and unambiguous orientation.

According to the present disclosure, an infusion device for infusion of a fluid from a replaceable reservoir (e.g., a carpule or ampoule) into a body is connectable to an infusion set adaptor at a connecting site of the infusion device, which connecting site can be located above an inserted carpule or at any other convenient location as long as a connecting element or cannula of the infusion set adaptor can be connected to or fluidly coupled with the substance or fluid to be infused. The infusion device comprises a drive mechanism, such as a motor with or without an encoder coupled to a gear system, bearings and optionally elements or sleeves to drive a driving element, such as a piston rod, to operatively couple with at least a portion of the exchangeable reservoir or carpule, which portion can, for example, be a plug slidably positioned within the carpule and causing the delivery of the substance or fluid contained within the carpule when pressed towards a delivery opening of the carpule. The infusion device comprises a housing which can be made of plastics or any other kind of material that is impermeable to water or is water resistant and further may be air tight. The housing may comprise a compartment or closed area which is at least partially or fully surrounded by a part of the housing, such as exterior or outer and inner housing walls, to protect the elements within this housing compartment from external influences, such as external liquids. The housing is formed or sized to contain at least a portion of the reservoir or carpule in a carpule compartment. The drive mechanism is at least partially or fully contained within the housing or contained within an enclosed compartment of or inside the housing. The drive mechanism compartment can be separated from the carpule compartment using separation elements, such as a drive housing and/or sealing elements or devices. An electronic control circuitry coupled to the drive system to control infusion of the fluid into the body and/or a battery compartment can also be arranged within the same compartment, e.g., the drive mechanism compartment or a different or further separate compartment inside the housing, so that the housing compartment or compartments enclose or surround at least a portion of the reservoir, separated therefrom, e.g., by an air permeable seal, at least a portion or all of the drive mechanism and optionally the control circuitry or the battery. A sealing device is provided which permits the passage of air into and out of the housing or from the interior to the exterior of the housing and vice versa or to the enclosed mentioned compartment(s) and inhibits the passage of liquids into the housing or the housing interior or into at least one of the enclosed compartment(s), such as the drive mechanism compartment. The sealing device can be a single element or can be several separate sealing elements and is arranged at the drive mechanism or a part thereof or at a location between a part of the drive mechanism and the connecting site of the infusion set adaptor or at the connecting site of the infusion set adaptor. The sealing device or one or more sealing elements of the sealing device may be located along a path through which air can flow or can be exchanged between the inside of the housing, such as the drive mechanism compartment, and the outside of the housing in order to seal this path and to prevent the intrusion of external liquid or water and also to prevent the leaking of a fluid to the outside of the housing. Any opening or path such as at the battery compartment, at a function key, at or around the display can be sealed with such a sealing element.

The sealing device or an element thereof which can be considered to be permeable for air may be arranged inside the housing, for example, between the carpule compartment and the drive mechanism compartment, but can also be arranged at an opening of the housing to the exterior, such as an opening provided in the housing to which an infusion set adaptor can be connected and/or at which a carpule can be inserted into the housing or can be exchanged or replaced.

The sealing device which permits the passage of air into and out of the housing or a housing compartment and inhibits the passage of liquids into the housing or a housing compartment through the sealing device can be arranged at or in any path from the inside of the housing or the housing compartment to the outside of the housing or to a neighboring compartment being on a path to the outside of the housing and can for example be a sealing device which will be present at any known location in any prior art infusion device, however, being modified or made from a material to permit the passage of air into and out of the housing or a housing compartment and inhibit the passage of liquids into the housing or a housing compartment. For example a sealing device being provided at an opening or surrounding the cover of a compartment, such as the cover of the battery compartment, can according to the invention be made to be air-permeable and liquid-impermeable. In addition or alternatively a sealing device provided at a function key, such as a sealing device for example surrounding the function key itself or encompassing a function key unit to shield the housing's interior can be made from a material being permeable for air and impermeable for liquids. Alternatively or in addition, a sealing device being provided to seal the gap or opening between the display and the neighboring housing can be made to be air-permeable and impermeable for liquids.

The sealing device or at least an element thereof may be arranged between an inner area of the infusion device in which inner area for example at least a part of or the whole drive mechanism and/or optionally one or more of the reservoir or carpule or electronic control circuitry or battery is located and which is enclosed by at least a part of the housing, which part can also comprise or be an internal and/or part or wall of the housing, and an outer area of the infusion device, wherein the carpule compartment or reservoir area of the infusion device can optionally or partly be seen as belonging to the outer area of the infusion device. Going from the outside or the exterior of the infusion device or housing to the inside, one may pass optionally a sealing device or an element thereof, the carpule compartment, optionally a sealing element, the drive mechanism, optionally a sealing element, optionally an electronic control circuitry and optionally a battery. The path from the outside to the inside needs not to be on a straight line and can be curved inside the housing and may have a "U"-shape, as shown in FIG. 2.

The drive mechanism may include a driving element, such as a motor being driven by electricity or other means, such as pressurized air. The drive mechanism may include a gear system connected to the motor including, e.g., gear system toothed wheels. A drive housing may be provided as part of the drive mechanism, which drive housing may separate the drive system compartment being interior of the pump from other compartments or the exterior. The drive housing may have an opening through which a driven element such as a piston rod may pass or advance.

In some implementations, the housing does not contain a vent port, such as, for example a vent port 8 shown in the enclosed FIG. 2 or a vent port as described in the mentioned U.S. Pat. No. 7,597,682 B2. However, optionally such a vent port can be provided in an infusion device according to the present invention, although such a vent port being an aperture of the housing with the sole purpose to permit the passage of air into and out of the housing or between the drive mechanism compartment and the carpule compartment is no longer required.

The sealing device or at least an element thereof may include or may be formed of a hydrophobic and/or lipophobic or oleophobic material that permits the passage of air into and out of the housing and inhibits the passage of liquids into the housing. Such a hydrophobic or lipophobic material can be formed from Polytetrafluoroethylene (PTFE), High-density polyethylene (HDPE), Polyethersulfon (PES), Ultra-high-molecular-weight polyethylene (UHMW) polymers and can, for example, be Gore-Tex®, Polyphobe™, Porex®, Filtrone, polyurethane foam or porous plastic.

The sealing device or at least a sealing element can be attached to the housing and/or to the infusion set adaptor using adhesives, sonic welding, heat welding or molding or any other method to provide an adhesive bond or a form fit.

The sealing device or a sealing element may accordingly allow the air pressure within the housing or within a compartment of the housing, such as the drive mechanism compartment, to equalize with the air pressure outside of the housing or a compartment on the path to the outside, such as the carpule compartment, for example, by permitting a certain amount of inside air to pass through the sealing device or sealing element to the outside or neighboring compartment in case the air pressure inside the housing is higher than that on the exterior side or vice versa in case the outside air pressure is higher than the pressure in the inside, which inside might be the compartment in which at least parts or all elements of the drive mechanism and/or optionally the carpule or electronic control circuit or battery is arranged. The air pressure equalization is thus not guaranteed by a separate opening in the housing but instead by the sealing device or sealing element being located along a path from the outside to the inside of the compartment or housing, as mentioned above.

The sealing device or a sealing element can be formed as an O-ring, a gasket ring or a seal ring or can have any other shape to seal the mentioned path from the outside to the inside of the housing. One or more sealing elements can be provided within or at the housing and/or within or at the infusion set adaptor.

A sealing element, such as a sealing ring or O-ring, can be provided between an inner side of the housing or an integral part of the housing, such as a viewing window, and a part of the drive mechanism, such as for example a drive housing, to permit the passage of air and to inhibit the passage of liquids. Another location for a seal may be on the carpule compartment, such as on the inner side thereof, which may be at a distal side of the carpule compartment, so that this seal may on the opposite inner side be in contact with a proximal housing of the infusion set adaptor when placed or fixed onto the infusion device.

A further location for the sealing element or the sealing device may be at the infusion set adaptor, such as on the outside of an outer wall of the proximal housing of the infusion set adaptor.

More than a single sealing element can form the sealing device and, for instance, two sealing elements or sealing rings may be provided at the adaptor and/or at the infusion device, e.g., at the above-mentioned locations and having an axial offset, such as being spaced apart in a dispensing or administering direction of the substance to be infused. It is also possible to combine the provision of a single or more sealing element at the infusion device and one or more sealing elements at the infusion set adaptor. In case two or more sealing elements are provided along a gas exchange path, all sealing elements may be permeable for air and at least one or all may be impermeable for water.

An infusion set adaptor according to the present invention is connectable to an infusion device for infusion of a fluid from a reservoir into a body, which infusion device can be any of the above-mentioned prior art infusion devices or infusion devices according to the present invention. The infusion set adaptor comprises a sealing device having at least a single sealing element which permits the passage of air into and out of the housing and inhibits the passage of liquids into the housing through the sealing device when the infusion set adaptor is connected to the infusion device. In case the carpule is inserted into the infusion device or needs to be replaced, the infusion set adaptor is removed from the infusion device, the insertion of the filled carpule takes place and then the infusion set adaptor is placed at the connecting site on the infusion device and may be locked with the infusion device, for example by a bayonet lock. The sealing element or sealing device is then arranged at a location which prevents in the state of the infusion set adaptor being connected to the infusion device that liquid can pass from the outside of the infusion device to the inside and thus shields or protects for example the drive mechanism and/or the carpule from getting into contact with liquids on the exterior side of the infusion device.

A method of equalizing pressure in an infusion device for infusion of a fluid from a reservoir into a body, the infusion device being connectable to an infusion set adaptor at a connecting site, the infusion device comprising a drive mechanism to operatively couple with at least a portion of the reservoir, a housing being sized to contain at least a portion or all of the drive mechanism comprises the step of: providing a seal in a path from inside the housing to the outside of the housing which seal permits the passage of air into and out of the housing or drive mechanism compartment and inhibits a passage of liquids into the housing to equalize the air pressure inside the housing with the air pressure outside of the housing.

BRIEF DESCRIPTION OF THE DRAWINGS

FIGS. 3*a-g* are representations of the drive train.

DETAILED DESCRIPTION

In order to specify the directions within the administering apparatus, designated directions are defined as follows. The distal direction is respectively understood to mean the direction in which the liquid and the drug plug are moved when the drug is administered. As will be described again in more detail below, liquid in the liquid path is diverted in the interior of the administering apparatus and changes its flow direction. The distal direction therefore corresponds to different absolute spatial directions for different parts of the administering device. The proximal direction is correspondingly defined as the opposite direction to the distal direction. A lateral direction is a direction perpendicular to this.

FIGS. 1 to 6 show an embodiment in accordance with the invention of the device for administering a fluid product. The embodiment shown in the figures is intended to describe the invention by way of an example. Other embodiments have already been described in part further above and/or are mentioned repeatedly in the text of the description of the figures, and additional possible embodiments will be apparent to the person skilled in the art on the basis of the description of the invention, such that the embodiments described below are not to be regarded as limiting.

Figure 1A:
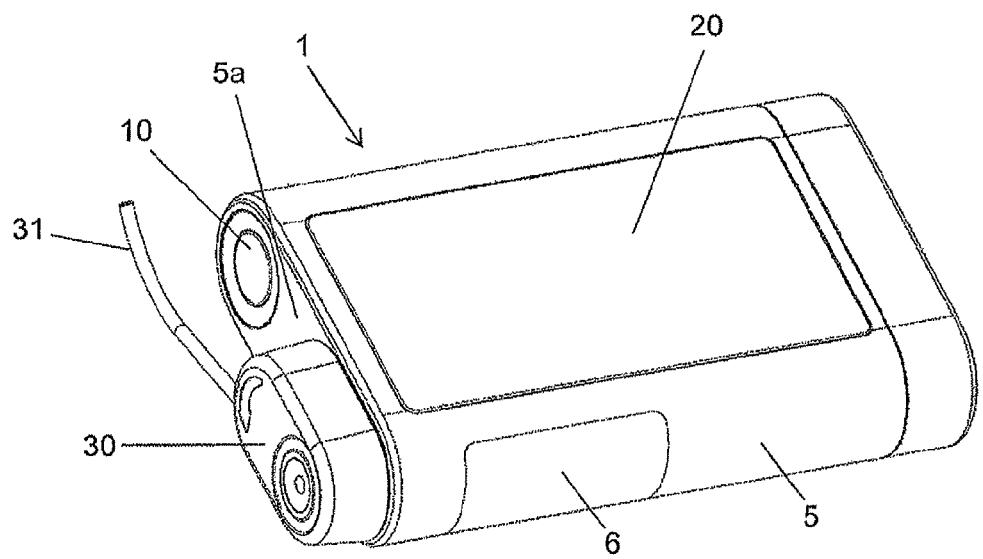
FIG. 1*a* is an exterior view of a device in accordance with the present disclosure.
Figure 1B:
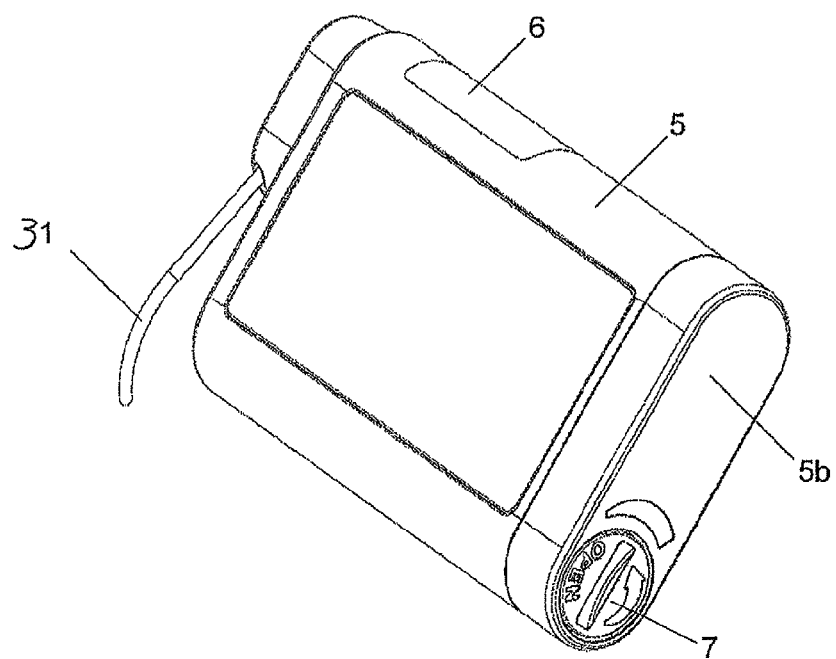
FIG. 1*b* is another exterior view of a device in accordance with the present disclosure.
Figure 2:
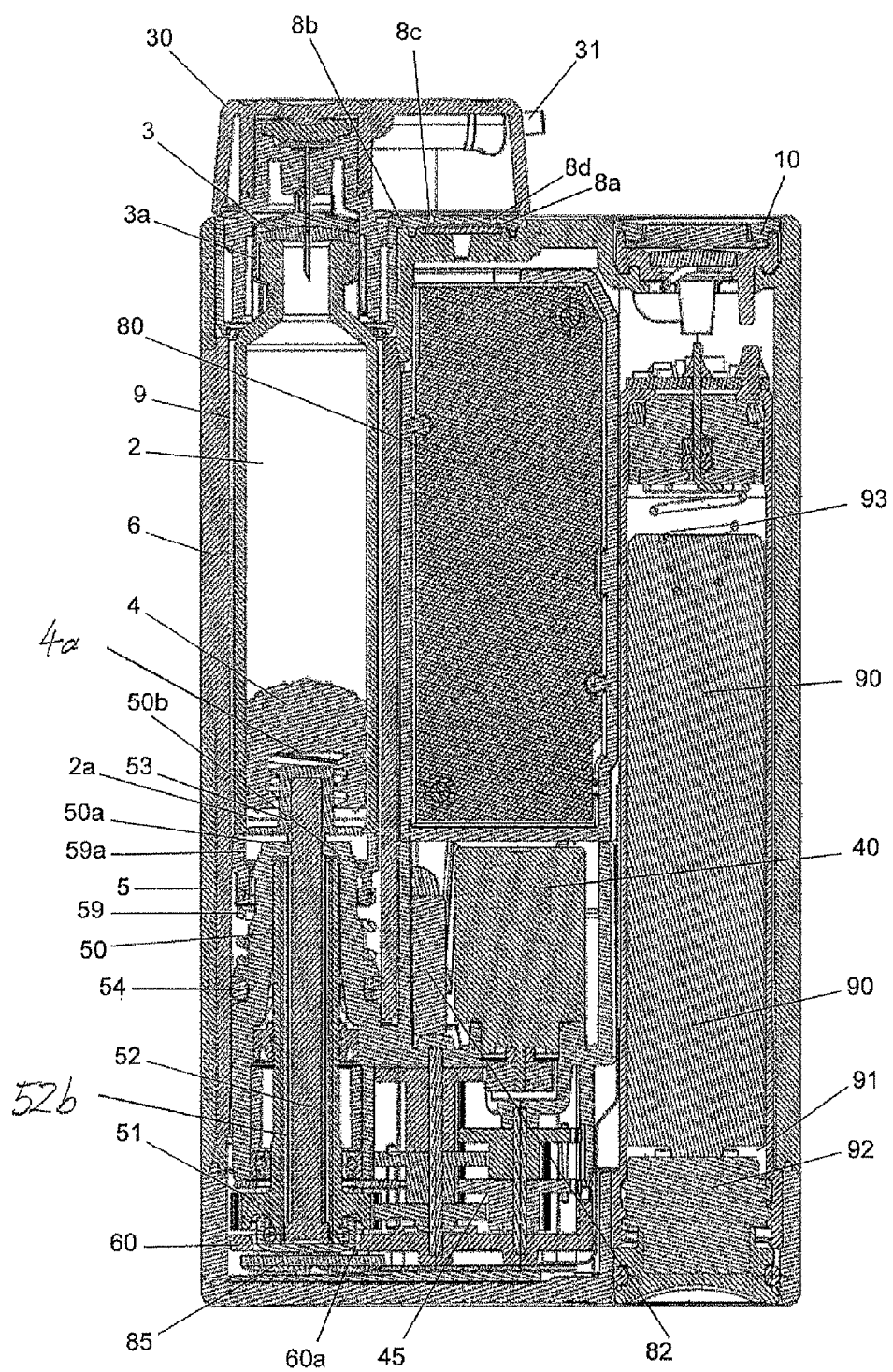
FIG. 2 is a cross-sectional view of the administering apparatus and the adaptor in accordance with the present disclosure.

The device shown in FIGS. 1a, 1b and 2 comprises the administering apparatus 1, shown here as an infusion pump, and the infusion set, wherein only the infusion set adaptor 30 and the infusion line 31 of the infusion set are shown. The front side of the administering apparatus 1 is shown in FIG. 1a, and the rear side in FIG. 1b. A touch display 20 is arranged on the front side and comprises at least a display device, in particular an OLED or AMOLED, and a touch-sensitive surface arranged over the display device, in particular a touch screen, wherein the touch display 20 is sunk into the housing 5 of the administering apparatus 1, such that it ideally forms a continuous and smooth surface with the surface of the housing 5, wherein the touch display 20 is adhered or fused to the housing 5 or at least joined to the housing 5 in such a way that the join is closed in a liquid-proof seal.

Figure 5:
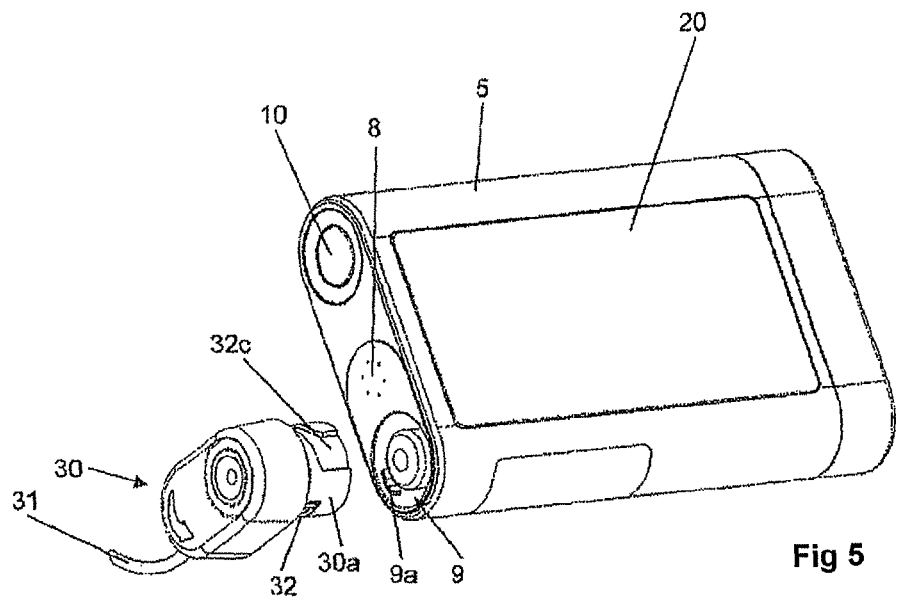
FIG. 5 is an isometric view of the adaptor and receiving compartment.

The viewing window 6 is arranged in a side wall of the housing 5 and can be an integral part of the housing 5 and enables the person using the device to view the carpule compartment 9. The function key 10 is arranged on the distal wall 5a. As shown in FIG. 5, other elements are arranged on the distal wall 5a, namely the opening of the carpule compartment 9 on the one hand and the device 8 for ventilating or evacuating the housing on the other. The latter enables the pressure to be equalized between the outside and inside of the administering apparatus 1. In the embodiment shown in FIG. 2, the ventilating or evacuating device 8 comprises a membrane 8a which closes an opening 8d of the housing. The membrane 8a allows gases to pass through but prevents liquid from passing through. The membrane 8a is protected against damage from without by the evacuating protection 8b. So as not to obstruct the exchange of gas between the inside and outside of the housing, the evacuating protection 8b comprises apertures 8c or holes.

FIG. 2 shows the carpule compartment 9 in section. The carpule compartment 9 serves to accommodate the product container—in the case shown, the carpule 2—wherein the carpule 2 is introduced into the carpule compartment 9 with its open end 2 first. The opening of the carpule compartment 9 is closed by means of the infusion set adaptor 30, as shown in FIG. 1a and FIG. 2. The opening of the battery compartment 91 is arranged in the proximal wall 5b. The opening of the battery compartment 91 can be closed and opened by means of the battery compartment lid 7, wherein the battery compartment lid 7 is formed such that it can close the battery compartment 91 in a water-proof but e.g. gas-permeable seal. The battery 90 can be introduced into the battery compartment 91, as shown in FIG. 2, wherein the primary cell 90 can be a commercially available AAA battery or alternatively a different type of battery or a correspondingly dimensioned rechargeable power pack. In order to obtain a good electrical contact between the battery 90 and the negative contact terminal 93 of the administering apparatus 1 and between the battery 90 and the positive contact terminal 92 of the administering apparatus 1, the negative terminal 93 can comprise or be formed as a spring, as shown in FIG. 2, wherein the positive terminal 92 is fixedly attached to the battery compartment lid 7, such that when the battery compartment 91 is closed, a pressure force which optimizes the electrical contacting is applied to the contacts by the spring force.

The administering apparatus 1 shown in FIGS. 1a, 1b and 2 comprises a drive device. The drive device, which is also shown in detail in FIGS. 3a to 3g, comprises a motor 40, a gear system 45, an advancing sleeve 51 and a piston rod 52. The drive device also comprises a drive housing 50 in and/or on which the parts of the drive device can be mounted, wherein the drive housing 50 is fixedly connected to the housing 5. The seals 54, 57 and 58 seal the drive device off from the carpule compartment 9 in a liquid-proof seal, in order to prevent liquid from crossing into the interior of the drive device. Seals 54, 57 and/or 58 can be made of a material which permits the transmission of air, as described above. The motor 40 is controlled and fed by an electronic control module 80. When activated, the motor axle 40a rotates and with it the driven toothed wheel 40b arranged rotationally fixed on the axle. The driven toothed wheel 40b transmits the movement onto the gear system 45. The movement of the motor is geared up or down in the desired ratio via the toothed wheels 45a to 45e of the gear system 45, wherein the toothed wheels 45a to 45e of the gear system 45 are rotatably mounted on the axles 45f and 45g, respectively.

The gear system toothed wheels 45a to 45e comprise two coaxially arranged toothings which are arranged sequentially in the axial direction and such that they are fixedly connected to each other, wherein the two toothings typically exhibit a different number of teeth. The first toothing assimilates the movement from the preceding toothed wheel. The second toothing relays the movement to the next toothed wheel, wherein—as the person skilled in the art will be aware—the embodiment of the gear system can vary without deviating from the concept of the invention. In particular, a different number of toothed wheels in the gear system can be chosen and/or the number of teeth on a toothed wheel can be varied. At the output of the gear system 45, the toothed wheel 45*e* transmits the movement onto the toothing 51*a* of the advancing sleeve 51. The advancing sleeve 51 is rotatably mounted in the drive housing 50 with the aid of the ball bearing 55, wherein a roll bearing, needle bearing or a simple slide bearing would also be possible. The seal 58 is arranged between the drive housing 50 and the advancing sleeve 51 and seals the interior of the drive housing 50 off from the outside of the rotatable advancing sleeve 51. On its inside, the advancing sleeve 51 comprises an inner thread 51*b* which is in engagement with an outer thread 52*b* of the piston rod 52. The piston rod 52 is arranged coaxially with respect to the advancing sleeve 51 and coupled to it via the threaded engagement mentioned. The piston rod 52 also comprises two longitudinal guiding grooves 52*a*. The cams 50*a* of the drive housing 50 engage with these guiding grooves 52*a* and thus allow a movement of the piston rod 52 in the longitudinal direction of the piston rod 52 relative to the drive housing 50, but prevent a relative rotation between the piston rod 52 and the drive housing 50. If the advancing sleeve 51 is rotationally set in motion via the gear system 45, then the threaded engagement between the advancing sleeve 51 and the piston rod 52 in combination with the rotational lock between the drive housing 50 and the piston rod 52 generates an axial shift in the piston rod 52 relative to the drive housing 50, hence the piston rod 52 is also shifted relative to the housing 5. During a movement for administering product, the piston rod 52 moves in the distal direction. The described arrangement of the drive can be kinematically reversed, without deviating from the teaching of the invention. In such a reversal, the piston rod 52 would be mounted, such that it can be shifted but is secured against rotating, in the advancing sleeve 51 and would be connected to the drive housing 50 via a threaded connection. If the advancing sleeve 51 were then rotationally set in motion by the gear system 45, the piston rod 52 would also be rotated and consequently screwed in the axial direction via the threaded connection with the drive housing 50. An equally advantageous axial advance by the piston rod 52 could thus also be achieved using a kinematically reversed arrangement.

A cap flange 53 is attached to the distal end of the piston rod 52 and can mechanically engage with the proximal end of a carpule plug 4. In the example from FIG. 2 shown, the proximal side of the carpule plug 4 comprises a piston rod receptacle as a blind hole 4*a* with an inner thread, which improves the engagement of the cap flange 53. In an equally advantageous embodiment, a carpule plug 4 with no blind hole 4*a* is also conceivable, wherein the shape of the cap flange 53 would be correspondingly adapted. As described above, the carpule 2 is arranged in the housing 5. When the infusion set adaptor 30 is inserted into the housing 5, the carpule 2 is mounted axially between the drive housing 50 and the infusion set adaptor 30, wherein a carpule spring 59 ensures, via a sleeve 59*a* which abuts the proximal end of the carpule wall, that the carpule 2 is pressed in the distal direction against the infusion set adaptor 30. The carpule 2 comprises a cylindrical body which is open at its proximal end 2*a* and tapers at its distal end and is closed by a septum 3, wherein the septum 3 is fastened to the distal end of the carpule 2 by a septum holder 3*a*. The carpule plug 4 is mounted, such that it can be axially shifted, in the carpule 2 and forms a moving proximal closure of the carpule 2, since it also forms a seal with the carpule wall. When the infusion set adaptor 30 is inserted into the housing 5, a connecting needle—shown as a cannula 33—pierces the septum 3 of the carpule 2 and thus establishes a liquid connection between the infusion set adaptor 30 and the interior space of the carpule 2, such that liquid product can pass from the carpule 2 into the infusion set adaptor 30. Shifting the carpule plug 4 by means of an axial movement of the piston rod 52 in the distal direction reduces the interior space of the carpule 2 and displaces product from the carpule 2 and thus conveys it into the infusion set adaptor 30.

As mentioned further above, the advancing sleeve 51 is rotatably mounted in the drive housing 50. Axial movements of the advancing sleeve 51 are possible to a limited extent. The axial movement is limited in the distal direction by the closed end 50*b* of the drive housing 50. The movement of the advancing sleeve 51 is limited in the proximal direction by a bearing plate 60 which is fixedly connected, in particular screwed, to the drive housing 50. A circular opening 60*a* arranged coaxially with respect to the advancing sleeve 51 is provided in the bearing plate 60 and exhibits a diameter which is less than the diameter of the region of the advancing sleeve 51 which bears the toothing 51*a*, thus ensuring that the axial movement of the advancing sleeve 51 is limited by the bearing plate 60, despite the opening 60*a*.

Figure 3G:
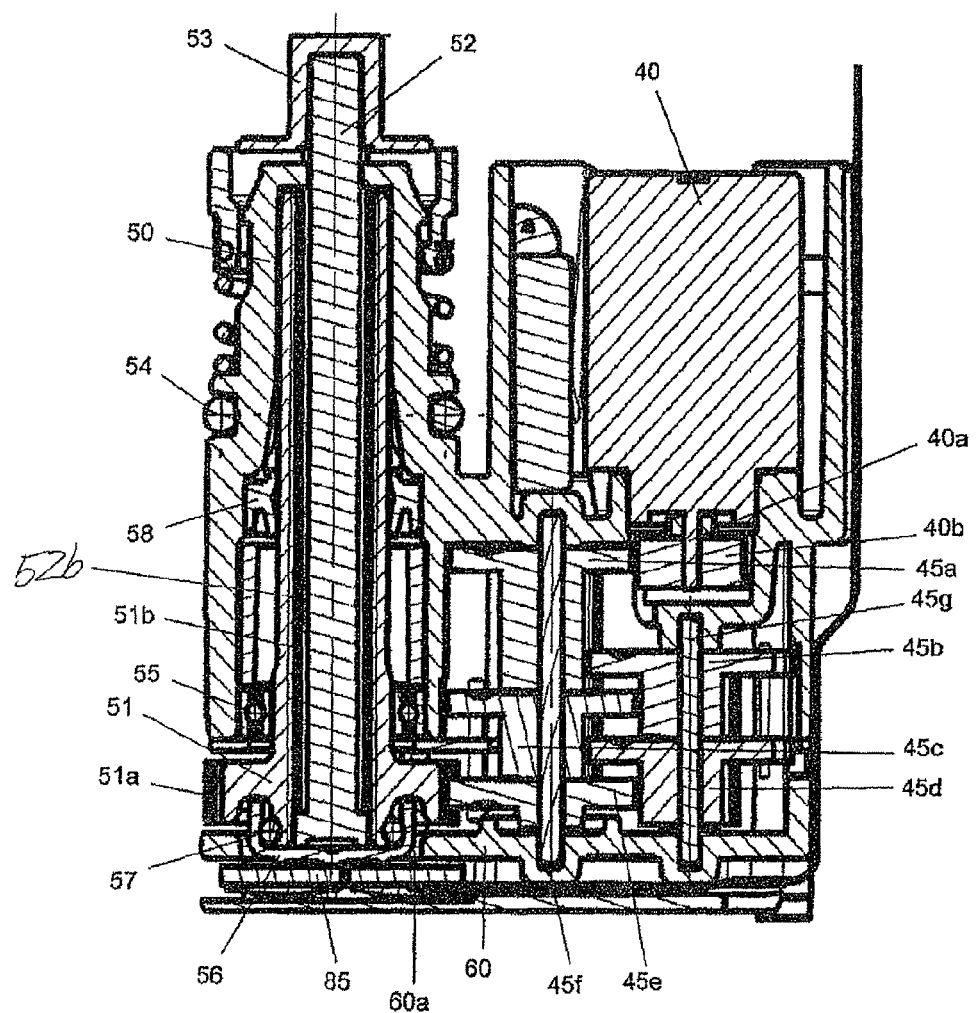

The proximal end of the advancing sleeve 51 is closed by the closure cap 56, wherein the closure cap 56 is movably held on the advancing sleeve 51 by the seal 57—shown for example in FIG. 3*g* as an O-ring—which is arranged on the proximal end of the advancing sleeve 51, wherein the diameter of the closure cap 56 is chosen such that the cap 56 fits through the opening 60*a* in the bearing plate 60. A force sensor 85 is arranged, fastened to the housing on one side, between the closure cap 56 and the housing 5 of the administering apparatus 1, wherein "fastened to the housing" means in particular that the force sensor 85 is mounted such that it cannot be moved laterally relative to the housing 5. A certain clearance can, but need not, be provided in the axial direction, but which is eliminated when the drive device is put into operation. Said force sensor 85 measures forces which are transmitted from the closure cap 56 to the sensor 85. Due to the advantageous embodiment of the closure cap 56, the advancing sleeve 51 and the piston rod 52, various forces can be measured using the arrangement shown in FIG. 2 or FIG. 3*g*.

On the one hand, the reaction force during the axial movement of the piston rod 52, in particular while product is being administered, can be measured, i.e., when the piston rod 52 is moved in the distal direction and presses against the carpule plug 4, the advancing sleeve 51 exerts a force in the proximal direction which is transmitted onto the force sensor 85 via the closure cap 56. Measuring forces in this way enables occlusions, i.e., for example blockages, in the infusion set to be identified on the basis of an increase in force and/or a force limit value during delivery, wherein the measurement signal generated in the force sensor 85 can be evaluated and stored in the control module 80. In addition, when carpules 2 are newly inserted, the position of the piston rod 52 at which the piston rod 52, in particular the cap flange 53, hits the carpule plug 4 can also be identified; in this situation, an increase in the reaction force can again be observed at the force sensor 85. The measurement signals from the force sensor 85 are read and evaluated by the control module 80. Consequently, the control module 80 can for example stop the motor 40 and issue alarm alerts on the display or let the motor 40 continue running. On the other hand, it is possible to measure forces which are transmitted directly from the piston rod 52 to the force sensor 85 via the closure cap 56. When a new carpule 2 is inserted into the administering apparatus 1, the piston rod 52 has to be moved back into its initial position before the new carpule 2 is inserted. This is achieved by driving the motor 40 in the opposite direction to the delivery movement. Consequently, the corresponding rotation of the advancing sleeve 51 draws the piston rod 52 into the advancing sleeve 51, i.e., in the proximal direction. When the piston rod 52 reaches its initial position, it hits the closure cap 56 and presses it in the proximal direction onto the force sensor 85. The increase in force which this generates can be measured by the sensor 85 and relayed to the control module 80. The control module 80 can then correspondingly stop the motor 40, and the new carpule 2 can be inserted.

The infusion set adaptor 30, including a proximal housing 30a and a distal housing 30b, can be detachably connected to the housing 5 of the administering apparatus 1. This may be achieved by the bayonet lock 32 shown in FIGS. 5 and 6. The bayonet lock 32 includes two guiding grooves 32b and 32c, which are arranged on the outside of the proximal housing 30a, and complementarily formed latching elements 9a (only one of which is shown in FIG. 5) in the carpule compartment 9. The guiding grooves 32b and 32c are of different widths, and the two latching elements 9a (only one of which is shown) are correspondingly also of different widths—to fit the groove width of the guiding grooves 32b and 32c, respectively. The proximal housing 30a of the infusion set adaptor 30 is formed such that it can be inserted into the carpule compartment 9 and such that a cylindrical fit between the proximal housing 30a and the carpule compartment 9 results. The latching elements 9a protrude in the radial direction into the interior of the carpule compartment 9 and are accommodated by the guiding grooves 32b and 32c, respectively, when the infusion set adaptor 30 is inserted and guide the movement of the infusion set adaptor 30. Due to the different widths of the guiding grooves 32b and 32c and the complementarily formed latching elements 9a, the infusion set adaptor 30 can only be inserted into the carpule compartment 9 in precisely one orientation. FIG. 5 shows the infusion set adaptor 30 and the administering apparatus 1 before the infusion set adaptor 30 is connected to the administering apparatus 1, wherein the infusion set adaptor 30 is already orientated such that it can be inserted into the carpule compartment 9. Once the infusion set adaptor 30 has been completely inserted, it is rotated in the present example by about 90° clockwise, in order to close the bayonet lock 32. This rotation is also guided by the correspondingly aligned grooves 32b and 32c which exhibit a corresponding bend. During this rotation, the infusion set adaptor 30 is drawn slightly further again into the carpule compartment 9, in order to generate an optimum closure. At the end of this rotation, the infusion set adaptor 30 is detachably snapped onto the carpule compartment 9 via latching cams 32a, in order to prevent the connection from being undesirably released, wherein a tactile or audible feedback which can be perceived by the person using the device may be generated during said snapping. The infusion set adaptor 30 may be configured so that it does not seal the carpule compartment 9 off in an air-tight manner, in order to allow pressure to be equalized between the carpule compartment 9 and the environment. In another embodiment, the rotational direction of the infusion set adaptor 30 can also be reversed, i.e., can be anti-clockwise. Correspondingly, the run of the grooves 32b and 32c of the bayonet lock 32 would also be aligned differently. The rotational angle can also be more or less than 90°, as long as the adaptor 30 can only be inserted into the carpule compartment 9 in precisely one orientation.

In the example shown, the proximal housing 30a and the distal housing 30b are adhered to each other in a water-proof seal. Alternatively, they could also be fused to each other.

Figure 4:
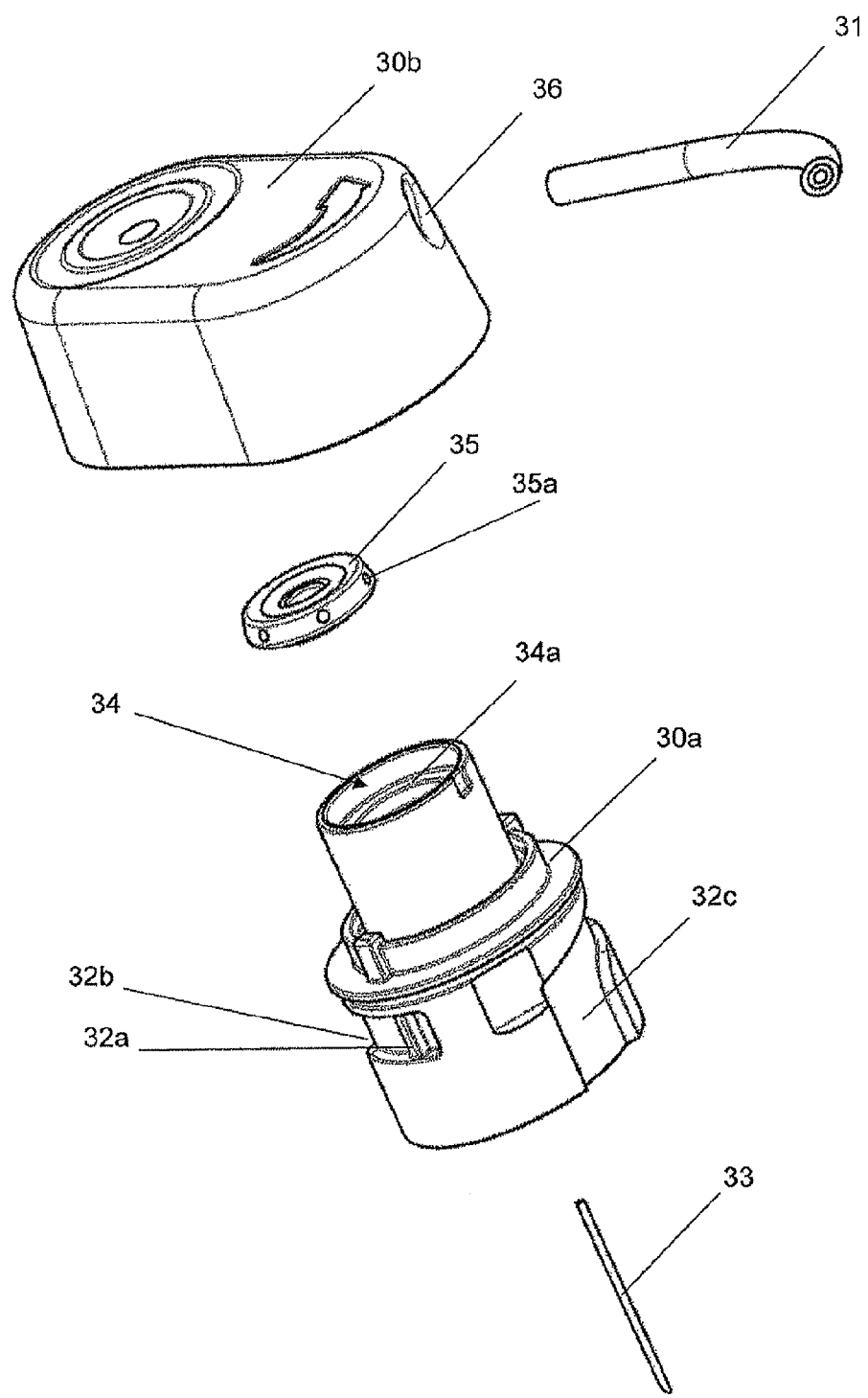
FIG. 4 is an exploded isometric view of the infusion set adaptor.
Figure 6:
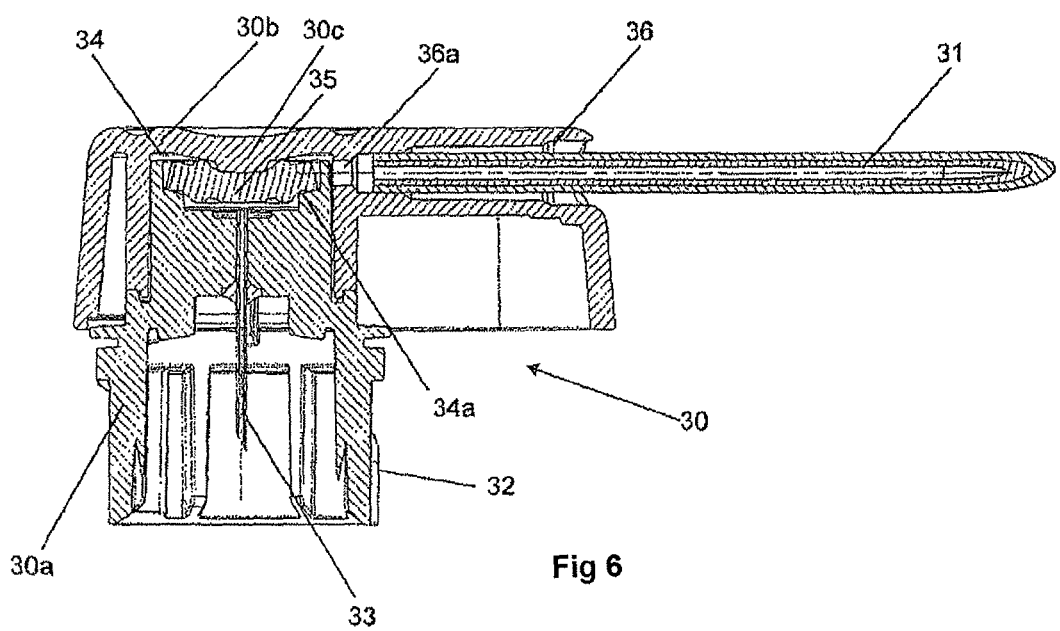
FIG. 6 is a cross-sectional view of the adaptor and the valve.

The infusion set adaptor 30 of the infusion set (which is not completely shown) establishes a liquid connection between the product container, corresponding to the carpule 2 shown, and the infusion set, shown here schematically as an infusion line 31. To this end, the infusion set adaptor 30 comprises a cannula 33 which serves to pierce the septum 3 of the carpule 2. The cannula 33 is arranged in the interior of the proximal housing 30a. The proximal housing 30a exhibits an approximately cylindrical shape and is open in the proximal direction. When the infusion set adaptor 30 is inserted into the carpule compartment 9 (and the bayonet lock 32 is latched), the proximal housing is arranged between the distal end of the carpule 2 and the wall of the carpule compartment 9. The cannula 33 is arranged coaxially with respect to the proximal housing 30a. When the infusion set adaptor 30 is inserted into the carpule compartment 9, the cannula 33 pierces the septum 3 of the carpule 2 which is inserted beforehand into the carpule compartment 9. This establishes a liquid connection between the carpule 2 and the interior of the infusion set adaptor 30. The infusion set adaptor 30 comprises a valve device 34, 35 which is arranged in the liquid path between the cannula 33 and the infusion line 31. The valve device 34, 35 has in principle two functions. Firstly, it is intended to prevent liquid from flowing back from the infusion line 31 into the administering apparatus 1. Secondly, product is to be prevented from undesirably flowing out, for example due to differences in pressure. While backflow is to be prevented completely, the flow of product for the purpose of administering product is to be possible, but only beyond a certain minimum pressure in the product container, wherein a compromise has to be drawn between safety (preventing product from undesirably flowing out) and obstructing the actual administering process as little as possible. The infusion line 31 typically has a length of 30 to 120 cm, which then corresponds to about the distance between the administering apparatus 1 and the administering location on the body of the person using the device. Assuming an unfavorable scenario, the difference in height between the administering apparatus 1 and the administering location may be roughly one meter, thus establishing a column of liquid having a corresponding height, which corresponds to a gravitational pressure of about 0.1 bar. As already mentioned, the carpule 2 comprises a carpule plug 4 which is movably mounted in the carpule 2. In order to deliver product from the carpule 2, the carpule plug 4 is pressed towards the septum 3, i.e., in the distal direction, by means of the piston rod 52 and the cap flange 53. The carpule plug 4 is not retained by the cap flange 53, i.e., the connection between the cap flange 53 and the plug 4 cannot absorb any tensile forces. If the friction between the carpule plug 4 and the carpule wall is sufficiently small that the difference in pressure just described can cause the plug to be shifted, then the drug will undesirably leak out. The carpule 2 has a typical inner diameter of about 9.25 mm; at a difference in pressure of 0.1 bar, a force of about 0.7 N can therefore act on the plug 4. EN ISO 11608-3:2000 specifies that the dynamic frictional force should not exceed 20 N and that the breakaway force of the carpule plug 4 should not exceed 40 N. In practice, however, the values are significantly lower, in the range of about 10 N or less. Frictional forces which are as low as possible are desired, so that as little drive energy as possible is lost through frictional losses. Optimizing the frictional forces, however, increases the risk of undesirable leakage in accordance with the rough calculation employed above. The valve device 34, takes account of this risk. In addition to the first function as a reflux valve, the valve device 34, 35 also functions as a threshold value valve. The valve is configured such that a typical (example) minimum pressure of about 0.3 bar in the product container has to be reached in order to open the valve and consequently enable the drug to be administered, wherein the minimum pressure can be tailored to a particular application. FIG. 4 shows the infusion set adaptor 30 in an exploded representation. FIG. 6 shows the infusion set adaptor 30 in a sectional representation, wherein the section is taken through the liquid path. The distal end of the cannula 33 feeds into a valve space 34. A valve membrane 35 is arranged in this valve space 34. On the right above the valve membrane 35, the valve space 34 feeds into the intersection 36a to the receptacle 36 for the infusion line 31. The infusion line 31, as well as the distal housing 30b of the infusion set adaptor 30, are embodied in materials, in particular plastic, which can be adhered or fused to each other—such that a liquid-proof connection is created. Alternatively, the receptacle 36 can also be embodied as a Luer cone, wherein the infusion line 31 comprises a corresponding counter-piece. The valve space 34 is designed so as to be rotationally symmetrical, in particular round, relative to the longitudinal axis of the cannula 33. The valve membrane 35 also comprises a round base area. The valve membrane 35 is clamped between the proximal housing 30a and the distal housing 30b, wherein the centering cam 30c of the distal housing 30b presses a central region of the valve membrane 35 in the proximal direction. The periphery of the valve membrane 35 lies on a sealing edge 34a of the valve space 34. Due to the pressure built up by the centering cam 30c and the corresponding elastic forces in the membrane 35, the liquid path is closed by the valve membrane 35 along the line of contact between the valve membrane 35 and the sealing edge 34a. The valve membrane 35 is made of a flexible material, for example rubber or another elastomeric material. The outside of the valve membrane 35 comprises the centering aids 35a which are important for assembling the infusion set adaptor 30, see FIG. 4 in this respect. For assembling, the valve membrane 35 is inserted into the distal end of the proximal housing 30a. The centering aids 35a, which in the form shown are formed as nubs 35a, enable the valve membrane 35 to be centrally positioned in the housing without consequently obstructing the transport of product through the infusion set adaptor 30 or impairing the valve characteristics due to the contact between the nubs 35a and the wall of the infusion set adaptor 30. As soon as the valve opens due to deformation of the valve membrane 35, the nubs 35a of the valve membrane 35 can no longer touch the wall of the infusion set adaptor 30 and thus do not influence the valve characteristics. In order to minimize the volume of the valve space 34, the wall of the distal housing 30b on which the centering cam 30c is arranged is shaped so as to be convex towards the valve space 34.

If pressure is built up on the proximal side of the valve membrane 35 and exceeds a particular threshold value, then the periphery of the valve membrane 35 is deflected in the distal direction and the valve opens in order for product to flow through it in the distal direction. If the pressure falls below the threshold value or a pressure burden is established on the distal side of the valve membrane, then the valve closes itself off, forming a seal, wherein the threshold value corresponds to the minimum pressure mentioned further above and is about 0.3 bars of relative pressure difference in the example shown.

In order to reduce the danger of the valve membrane 35 sticking to the sealing edge 34a, the valve membrane 35 in one advantageous embodiment does not completely close at pressures less than 0.3 bar. To this end, a small, defined leakage in the form of a micro-channel or micro-notch (not shown) is arranged on the sealing edge 34a, wherein the leakage is dimensioned to be sufficiently small that at the differences in pressure mentioned above, the greatest amount of product per unit time which can leak out is one which is harmless to the person using the device. Taking the example of insulin, this would mean a worst-case flow rate of 5 units of insulin per day. In this case, the leakage would exhibit a cross-sectional diameter of roughly 10 to 15 μm. Since half the diameter to the fourth power features in the Hagen-Poiseuille flow equation using which the flow rate is estimated, the greatest attention must be paid to the precise dimensioning of the leakage diameter. The defined leakage in the valve device 34, 35 has the advantage that, due to the defined leakage, minimal amounts of product can flow out even when the threshold value of the drive pressure has not yet been reached, which enables the valve device 34, 35 to be prevented from drying out completely. This embodiment presupposes that the product to be administered is compatible with the micro-leakage. Suspensions may for example impair the functionality of the leakage.

The administering device can be programmed and controlled by the person using the device. To this end, the administering apparatus 1 comprises a touch display 20 and a function key 10, both of which are connected to the control module 80. The control module 80 can display a menu structure on the touch display 20. The person using the device can control the administering apparatus 1 or also for example retrieve and display the administering "history" via the touch-sensitive touch display 20, with the aid of a finger or suitable pointer and the support of the menu structure. The person using the device can also program the types of administering. The person using the device can for example store a basal rate profile in the apparatus 1, which then controls how product is administered, in a time-controlled way. It is also possible for boluses to be dispensed immediately or with a time delay. As an alternative or complement to controlling the administering device via the touch display 20, a simplified form of control via the function key 10 is possible. In one function, the function key 10 serves as an on/off key or as a standby key. In another function, the function key 10 serves as a programming and triggering key for so-called blind boluses, i.e. activating the administering device to dispense boluses without the administering device having to be controlled via the touch display 20. This is advantageous because the person using the device can wear the administering apparatus 1, hidden from other people, while programming and triggering blind boluses. The boluses can thus be discreetly programmed and triggered. In order to acknowledge inputs or accentuate alerts, the administering apparatus 1 also comprises a vibration device 82 and a buzzer or loudspeaker (not shown). When programming and administering blind boluses, the vibration device 82 in particular can discreetly provide the person using the device with feedback regarding the bolus amount set, namely with a particular number of vibration pulses, and that the bolus has been successfully administered.

With respect to controlling the touch display 20 by means of a finger, it is also conceivable in one embodiment for gestures using multiple fingers simultaneously to be recorded by the touch display 20. Such gestures are known from the literature as multi-touch gestures.

Figure 7:
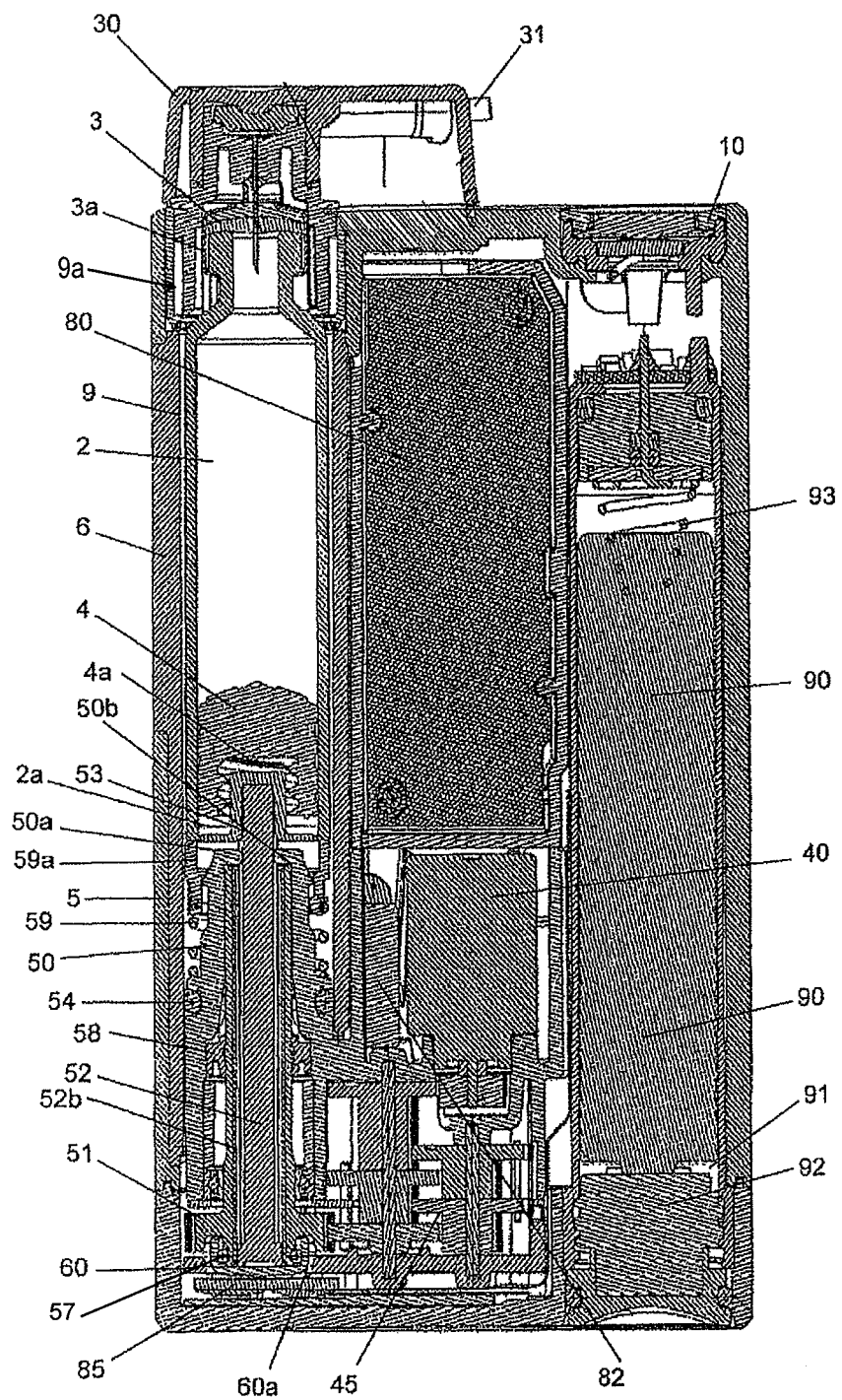
FIG. 7 is a cross-sectional view of an embodiment of an infusion device according to the present disclosure.

FIG. 7 shows an embodiment of the present invention, wherein reference is made to the above description of FIG. 2. The embodiment shown in FIG. 7 does not comprise the housing evacuator 8, the evacuating element 8*a*, the evacuating protection 8*b*, the aperture 8*c* and has no housing opening 8*d*. The only way to connect the inside of the housing 5, in which the battery 80 and the drive mechanism 40, 45, 50, 51, 52, 53, 55 and 56 is arranged, to the outside of the infusion device by allowing the passage of air is through seal 54 and optionally also through seal 57 and/or 58, which seal 54 is located between an element of the drive mechanism, such as for example the shown drive housing 50 being on the inner side of seal ring 54, and viewing window 6 or housing 5 being on the outside of seal ring 54. Seal 54 is made from a material allowing the passage of air and inhibiting the passage of liquids or water and may be in tight contact or bonded to the housing 5, 6 and to the drive housing 50 so that no unsealed opening is present between the housing compartment and the carpule compartment 9.

As mentioned above, seal or O-ring 54 can for example be made of PTFE, HDPE, PES, UHMW polymers or Gore-Tex®, Porex®, Polyphobe™ or Filtrone.

Figure 8:
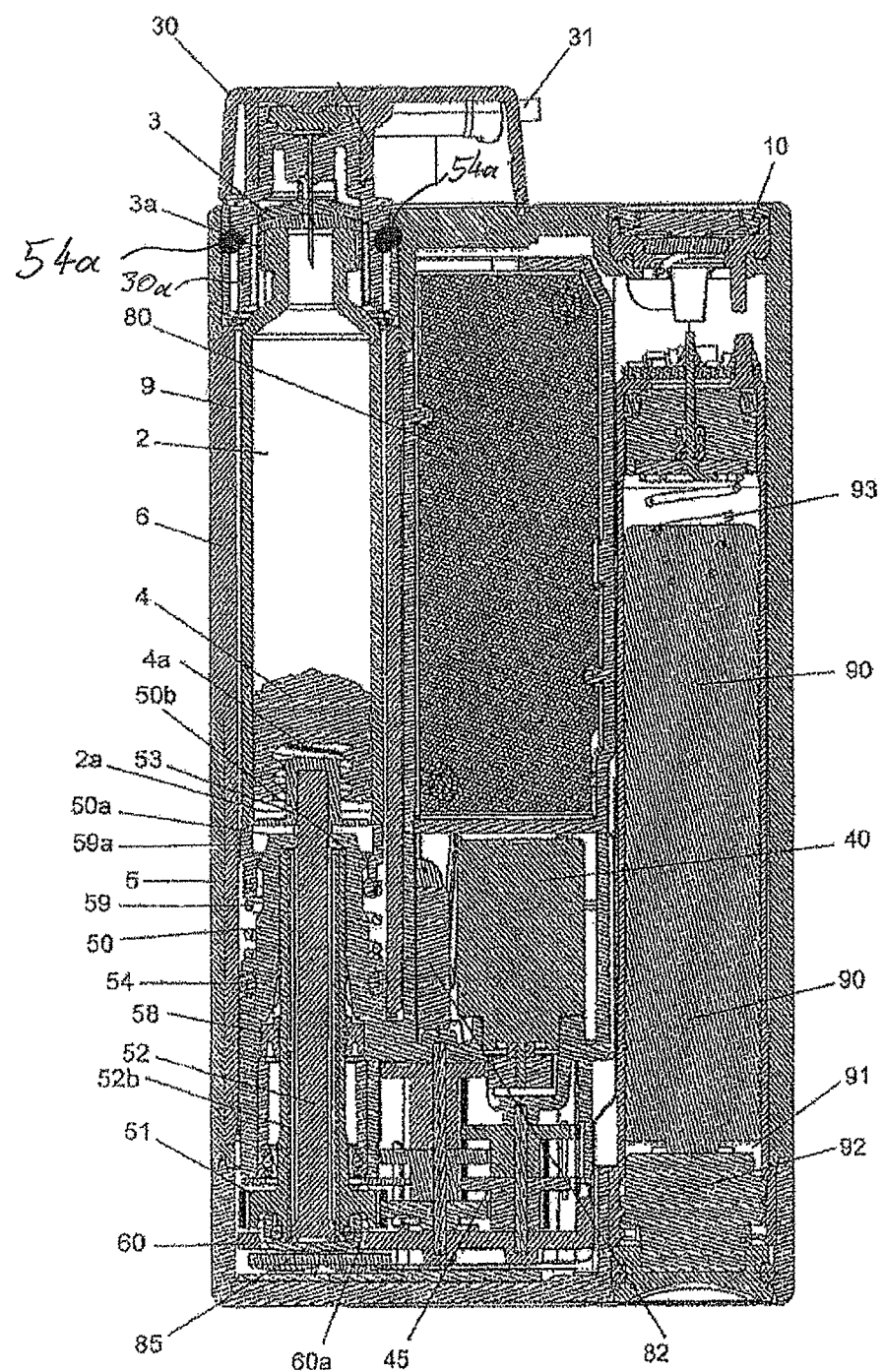
FIG. 8 is a cross-sectional view of a further embodiment of an infusion device according to the present disclosure.

FIG. 8 shows a further embodiment according to the present invention, wherein seal 54 can be made from a material allowing the passage of air and inhibiting the passage of liquids or water or can be a conventional seal. A further location for a seal 54*a* is shown on the upper or distal side of the housing 5. Seal 54*a* is attached on the inner side or side wall 9*a* (see FIG. 7) of the carpule compartment 9 to be in contact with the housing 30*a* of the infusion set adaptor 30 as mentioned above, when the infusion set adaptor 30 is placed onto the infusion device.

Figure 9:
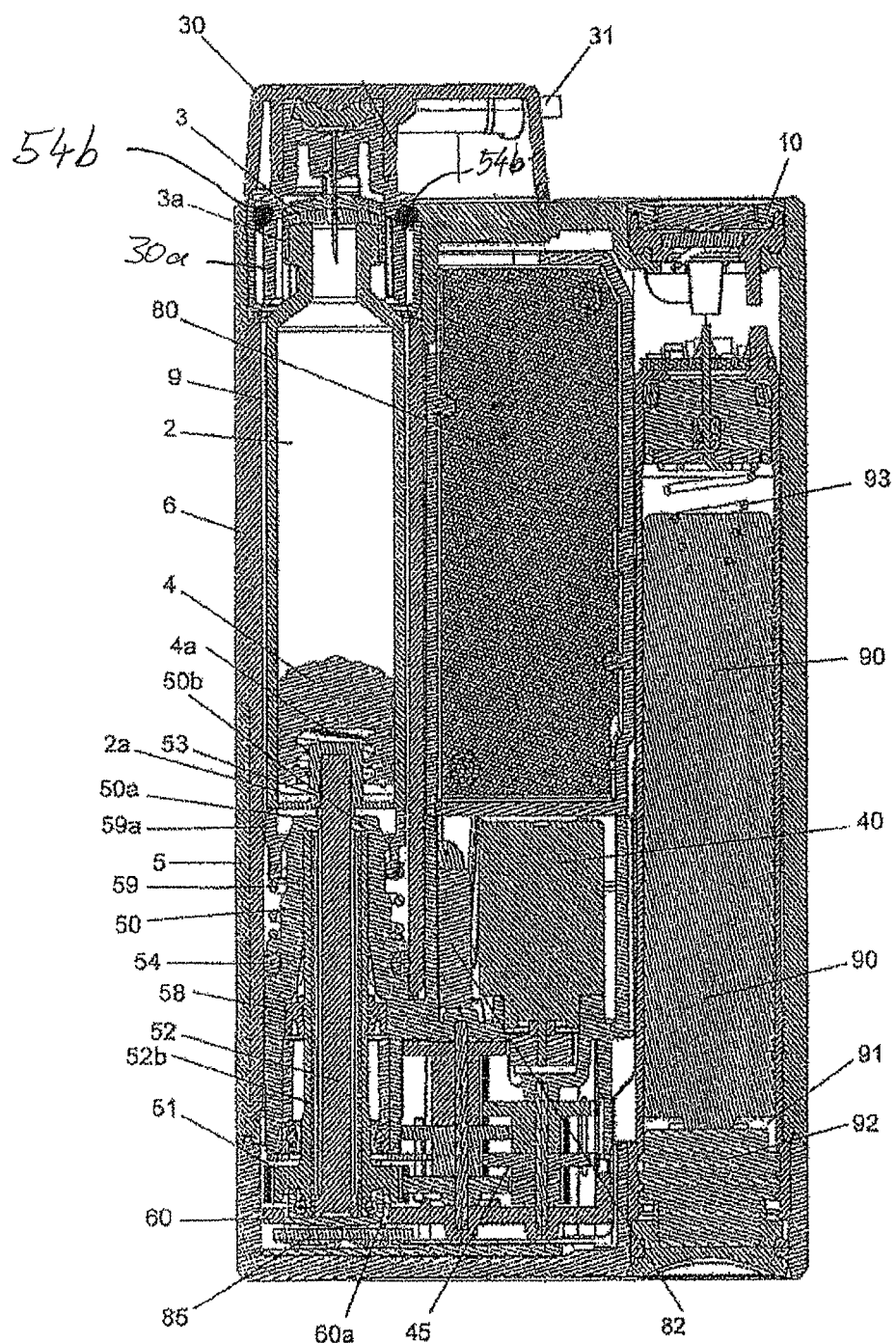
FIG. 9 a cross-sectional view of yet a further embodiment of an infusion device according to the present disclosure.

FIG. 9 shows a further embodiment of the invention, wherein seal 54*b* being made from a material allowing the passage of air and inhibiting the passage of liquids or water and being a seal ring is attached to the outside of the proximal housing 30*a* of the infusion set adaptor 30 and is brought into a position to be in contact with the inner wall 9*a* (see FIG. 7) of the carpule compartment 9 once the infusion set adaptor 30 is placed onto the infusion device 1.

Figure 10:
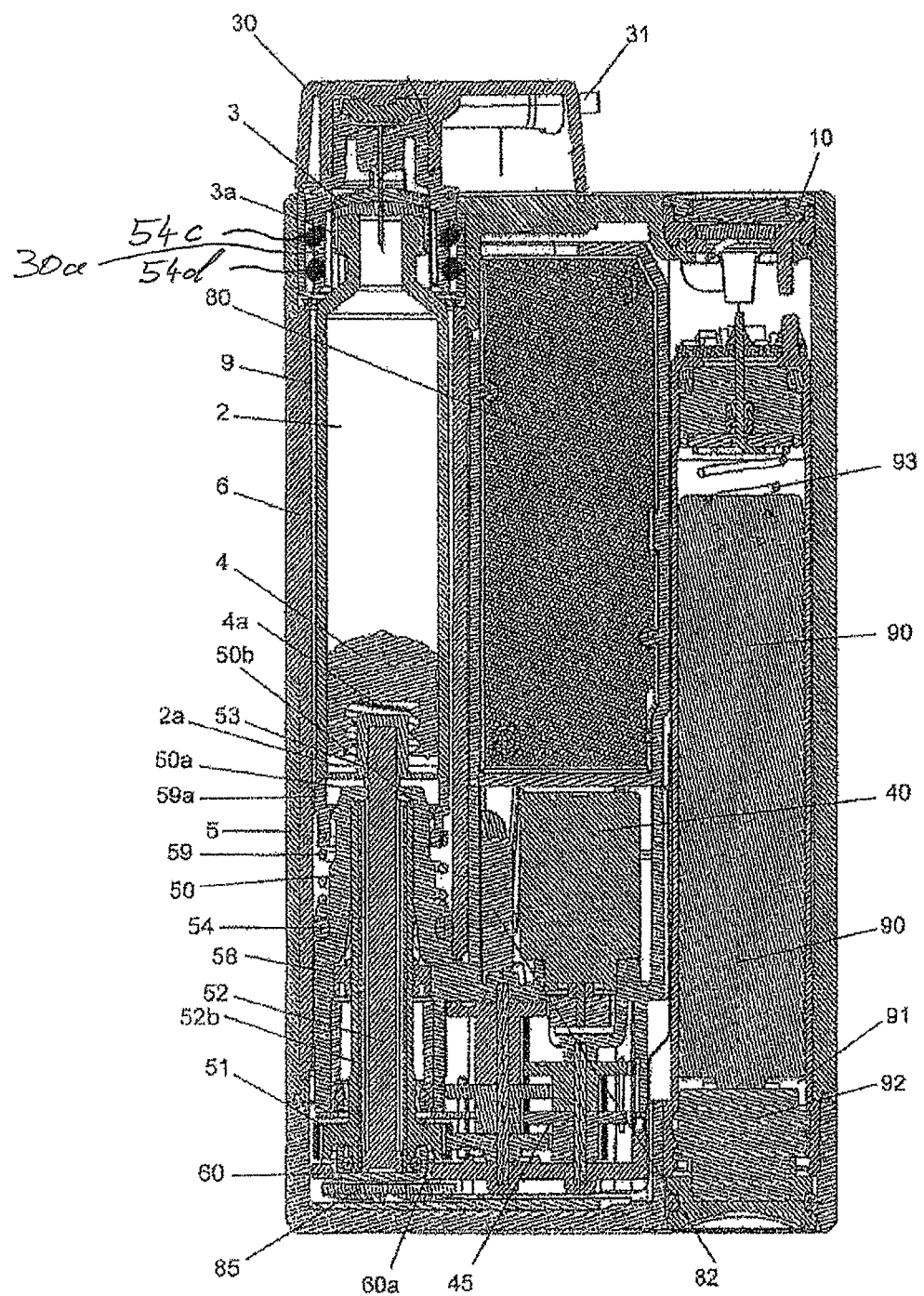
FIG. 10 a cross-sectional view of still a further embodiment of an infusion device according to the present disclosure.

FIG. 10 shows a further embodiment wherein two sealing elements 54*c* and 54*d* both being made from a material allowing the passage of air and inhibiting the passage of liquids or water and being sealing rings are attached to the outside or outer circumference of the proximal housing 30*a* of the infusion set adaptor 30 to be in contact with the inside or inner wall 9*a* (see FIG. 7) of the carpule compartment 9 when being placed thereon.

The invention relates according to a further aspect to an infusion set adaptor 30 for an infusion set, comprising: a housing 30*a*, 30*b*; a liquid path which extends through the housing 30*a*, 30*b* and comprises a liquid inlet 33 and a liquid outlet 36; and a membrane valve 34, 35 which is arranged in the liquid path and comprises an inlet and an outlet, wherein the membrane valve 34, 35 comprises a valve space 34, which is limited by walls, and a valve membrane 35, and wherein a valve seating 34 onto which the valve membrane 35 can be placed is arranged in the valve space 34, characterized in that at least two centering aids 35*a* are arranged on the walls or the periphery of the valve membrane 35 and in particular simplify centrally positioning the valve membrane 35 on the valve seating 34*a* when assembling the infusion set adaptor 30.

The infusion set adaptor 30 for an infusion set as described above, wherein the valve membrane 35 comprises the centering aids 35*a* at its periphery as radially aligned and nub-shaped centering aids 35*a*.

The infusion set adaptor 30 for an infusion set as described above, wherein the housing 30*a*, 30*b* comprises a proximal housing 30*a* and a distal housing 30*b*, wherein the liquid outlet 36 is arranged on the distal housing 30*b* and the liquid inlet 33 is arranged on the proximal housing 30*a*.

The infusion set adaptor 30 for an infusion set as described above, wherein the walls of the valve space 34 are formed by the proximal housing 30*a* and the distal housing 30*b*.

The infusion set adaptor 30 for an infusion set as described above, wherein the valve membrane 35 is shaped as a circular disc and, when assembling the infusion set adaptor 30, can be inserted into a space in the proximal housing 30*a* which is shaped complementarily with respect to the disc, wherein when the membrane 35 is not mechanically stressed, the centering aids 35*a* can touch a wall of the complementarily shaped space.

A device for administering a fluid product, comprising an administering apparatus 1 and an infusion set, wherein the infusion set can be detachably connected to the administering apparatus 1 by means of an infusion set adaptor 30 as described above, such that a liquid path between the infusion set and the administering apparatus 1 is created.

A device for administering a fluid product, comprising an administering apparatus and an infusion set, wherein the infusion set can be detachably connected to the administering apparatus by means of an infusion set adaptor, such that a liquid path between the infusion set and the administering apparatus is created. The infusion set adaptor comprises a membrane valve, wherein the membrane valve comprises centering aids for simplifying the positioning of the membrane.

Figure 11:
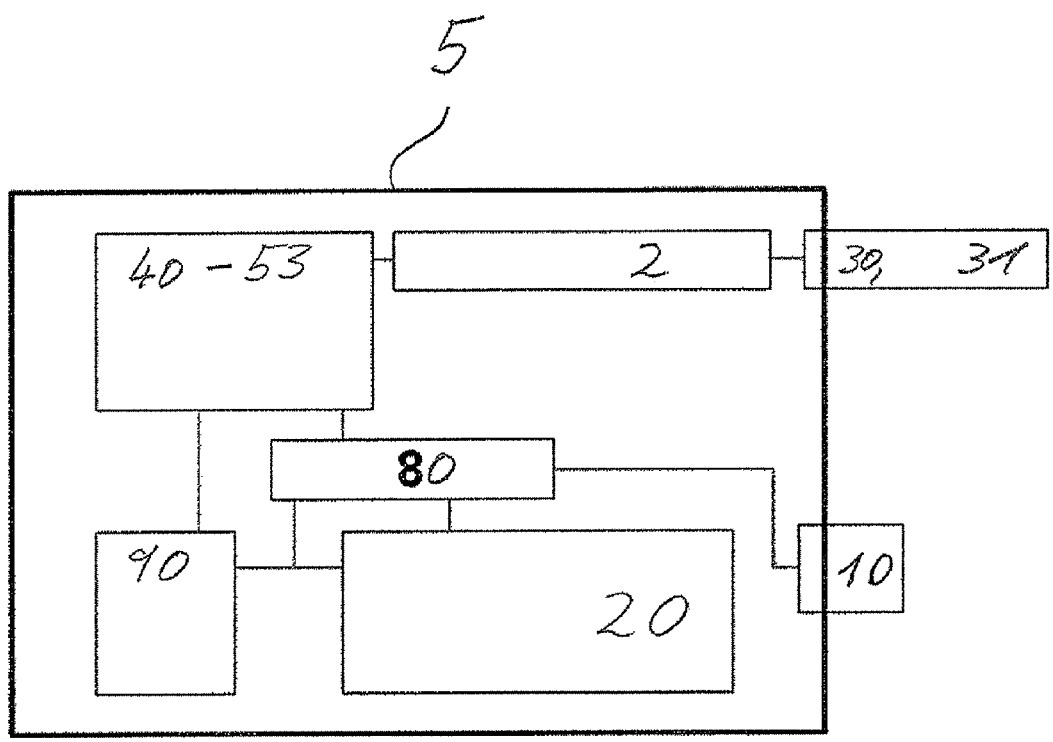
FIG. 11 is a block diagram of an infusion system according to the present disclosure.

FIG. 11 relates to a further aspect.

One common therapy for treating auto-immune diseases (for example, type 1 diabetes) involves near-continuously supplying a drug (for example, insulin) for the entire duration of the therapy, with the aid of a portable pump. In the case of diabetes, the pump therapy enables a (variable) basal rate of insulin to be continuously dispensed, as well as individual boluses which are employed in connection with mealtimes and for correcting excessively high glucose values in the patient's blood. By continuously dispensing the basal rate in accordance with a user-specific basal rate profile, a more uniform blood sugar level is achieved and the patient's organism is thus unburdened. Infusion systems are correspondingly known which include an infusion pump for insulin (insulin pump), a supply line to the body (infusion set) and, as applicable, a remote control. In general, the insulin pump is to be formed so as to be as compact as possible, so that it is not too bulky and is comfortable for the user to wear. The pump thus comprises a small pump housing which accommodates a battery, a motor including a gear system and control and communications electronics, and an ampoule which is connected to the infusion tube, forming a seal. The outside of the pump comprises operating keys and in most cases a display. This display, as well as the size and number of the operating keys, is limited by the structural shape which is to be realized. At the same time, operating them should be as simple and intuitive as possible, so that the users of the infusion system can perform the therapy themselves.

The conventional displays and keys which have been used hitherto result in solutions involving confusing displays and/or complicated operating steps using various keys. Modern touch displays, such as are used in smartphones, make them simpler to operate and clearer, but can hardly be entertained in insulin pumps for reasons of price and space and power consumption. This approach has hitherto only been pursued in remote controls.

Moreover, the requirement that it also be possible to administer a bolus "blind" necessitates the use of keys. The subject of the invention is therefore a concept for realizing a simple and clear way of operating infusion pumps, based on a touch display which exhibits a simple functionality, and an individual and in particular mechanical bolus key.

It is a further object of the invention to provide an infusion pump, and a method for controlling a user interface of such a system, which enable a large range of functions and a simple mode of operation, even when using miniaturized components.

This object is solved by an administering apparatus, in particular a portable infusion pump comprising a touch-sensitive display and an additional operating element, characterized in that the operating element is a key.

The touch-sensitive display can be a touch display or touch screen.

The touch screen or touch display can comprise 128×256 pixels at most.

The administering apparatus can comprise precisely one single additional operating element.

The precisely one or single additional operating element can be a mechanical key.

The precisely one or single additional operating element can be an electromechanical key.

The precisely one or single additional operating element can be a piezo-resistive key.

A feedback device can be provided at or in the administering apparatus, which feedback device can generate a tactile, acoustic or optical feedback as a response to the additional operating element being operated.

In one example embodiment, four concepts interact which are realized by the components mentioned: an operating concept comprising a touch display, i.e. a touch-sensitive display, and a single operating element, in particular a single mechanical key; an infusion set comprising an integrated pressure valve and a carpule adaptor; a drive concept comprising a deflection gear system and an integrated monitor; and a feed concept comprising a supporting power pack. Each of these concepts exhibits particular features in detail, which in their entirety result in a mode of operation which is substantially simplified as compared to conventional infusion pumps, but at the same time can be miniaturized.

The operating concept is characterized by: a display of 128×256 pixels at most; a gesture recognition system, in particular a capacitive gesture recognition system, which recognizes taps and swiping movements made by an individual finger; and an individual and in particular mechanical key which on the one hand enables the touch display to be activated and on the other hand enables a bolus to be programmed without using the display.

During normal operation, the display is switched off. It is activated by a keystroke and displays a summary of the current status. A swiping movement switches to a menu displaying a row of symbols. The symbols/sub-menus can be moved in and out of the visible region by left and right swiping movements, and selected by tapping them. The submenus are functional displays or screens which show displaying and setting options depending on the function. A keystroke cancels an initiated input and returns to the next respectively higher level. The operating concept described here can be implemented in both landscape and portrait format.

It is also possible to program a "blind" bolus using the key, which is in particular a mechanical key, thus circumventing the touch display, wherein a bolus is triggered without the need for eye contact or interaction with the display, for example while carrying the pump in one's trouser pocket or wearing it beneath one's clothing. To this end, the key is sequentially operated as follows:

1. a long keystroke, in order to activate the blind bolus function;
2. short keystrokes, acknowledged by tactilely perceivable signals from the pump, in order to input the bolus amount in predefined incremental increases;
3. a pause, upon which the pump system acknowledges the programmed amount, via tactile signals, and delivery then commences; and
4. any keystroke during delivery cancels the current delivery.

This series of keystrokes realizes a very simple mode of operation, with a very high level of security against unintentionally triggering the delivery of a bolus.

In accordance with the invention, the infusion set includes the following elements: a carpule connector; a pressure valve; and a transition line into the patient's body. The result of integrating these elements is that the infusion system is simpler and more secure to operate. In particular, it enables incompletely filled carpules to be used, a warning to be issued when the system is put into operation with no carpule, and the operation of the system to be monitored during delivery.

In accordance with the invention, the drive concept comprising a deflection gear system and an integrated monitor include: a drive comprising a rotary position monitor (encoder); a force transmission, arranged parallel thereto, onto the carpule stopper; and a deflection gear system which deflects the rotational movement of the drive and at the same time converts it into a linear thrust, wherein the deflection gear system is integrated into the pump housing in such a way that the force exerted on the carpule stopper can be measured using a force sensor. This arrangement enables a shorter and therefore more user-friendly structural shape of the pump system.

The feed concept comprising a supporting power pack includes a primary and a secondary energy source and a controller. The primary energy source is exchangeable and chosen such that it is as simple as possible for the user to replace (standard AAA or AAAA battery, operated without any special tools). The secondary energy source is fixedly installed, rechargeable and fed from the primary cell. This means on the one hand that the primary cell can be exchanged without interrupting the therapy, and on the other hand enables a warning to still be issued if the primary cell fails or an internal line is cut. The arrangement described thus enables a very simple mode of operation and at the same time the highest level of operational security.

The components of the infusion system shown in FIG. 11 are a housing 5, a mechanical drive 40-53, an energy source 90, a drug reservoir 2, a transition line to the patient's body (infusion set 30, 31), a touch-sensitive display or touch display 20, a key 10 and a controller 80.

Figure 12:
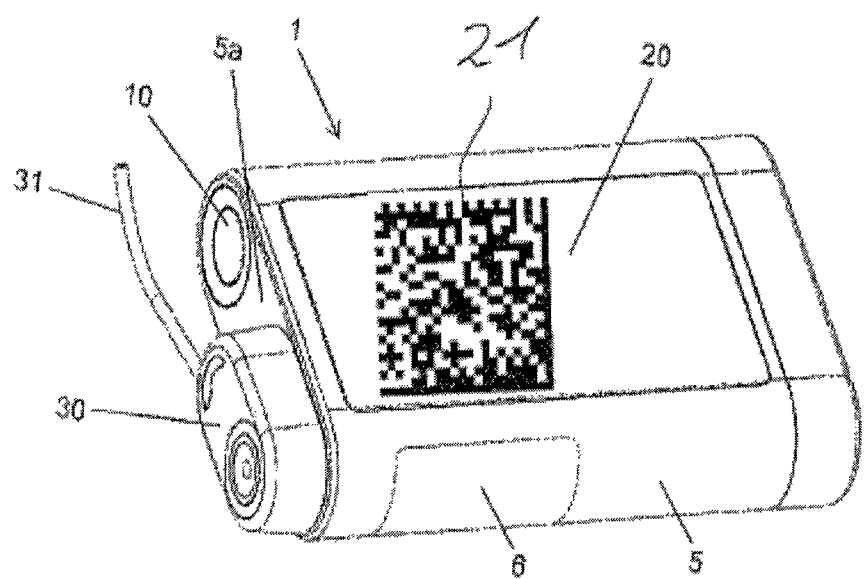
FIG. 12 is a separate embodiment of an infusion device according to the present disclosure.

FIG. 12 shows a further aspect being an infusion pump having a display 20 being able to display a code, such as a data matrix code 21. This data matrix code can be Data Matrix ECC 200 (a well-known error checking and correction algorithm). The data shown or encoded by the data matrix 21 can comprise or include data concerning the infusion pump itself and/or data concerning the functioning or working of the infusion pump, such as the infusion pump history. Data included in the infusion pump history can for example be data indicating what amount of medication was delivered over time, such as data concerning the basal rate and data concerning one or more boluses delivered by the infusion pump.

This infusion device can be combined with the above described aspects or can be independent thereof.

The displayed code can be a bar code instead of the mentioned matrix code and can be any readable code which is able to display information or to transfer information from inside the infusion device, such as information from a memory and/or processor 80 inside the infusion device to the display 20. The encoded information displayed on the display device can be read with an appropriate reading device having a camera, such as a mobile telephone, a camera connected to a computer or any other kind of camera connected to an electronic device.

Such a display can also be provided at a medical measuring device, such as at a blood glucose measuring device. In this case the data provided by the blood glucose measuring device and the data provided by the infusion pump can both be read by a camera and can be associated with each other using an electronic device.

The data graphically displayed on the display 20 can provide a serial communication where a sequence of information, for example a sequence of matrix codes or bar codes or pixels, e.g. a single blinking pixel, can be displayed. Each single code of the sequence can be displayed for a predetermined amount of time, such as for one second, whereafter the next code of the sequence is displayed until the last code required to transmit or display the desired information is reached. This displayed sequence of codes can be scanned by the mentioned camera connected to an electronic device which is able to extract the information from the displayed sequence of codes.

In case a single pixel is used, the display and the viewing or receiving device act as optocouplers. It is possible to provide a parallel communication on the display, which parallel communication can be provided using a clock signal and several data pixels or picture elements or picture areas. The display can for example be divided into a predetermined number of fields, such as for example into four, nine or 16 fields. Each field can then transmit a specific type of information by displaying a single picture or single data code or by providing a serial communication as described above, such as by providing a sequence of graphical codes.

To provide a scannable graphical code the infusion pump includes a graphical code generator, which can be included or be a part of the electronic control module 80 or can be a separate device, which is provided from an internal electronic device of the infusion pump, such as a processor which can be connected to a memory device, with the information to be transformed into the graphical code, matrix code or bar code by the code generator. The input data can be configuration data of the infusion pump, device data, system state data and infusion or delivery history data.

The code generator is connected to a display 20 for displaying the code, which display can be a transmissive display, such as a backlit LCD display, or can be a regular LCD display or can be a reflective display, such as an electronic paper.

The graphical code can be a bar code or a data matrix code 21 and can in general be any kind of code which is able to transport or transfer information once the code is displayed.

The scanning device can include electronics to obtain the information included in the scanned graphical code. According to an embodiment, an appropriate configured scanning device, such as a mobile phone or computer, can include a browser able to view a given web page associated with an Uniform Resource Locator (URL) included in the displayed graphical code and can display the contents of the thus specified web page.

The information included in the graphical code can specify a particular alarm of the infusion pump or indicate malfunction and optionally data associated with the malfunction, such as data specifying the pressure detected by an internal pressure sensor of the infusion pump in case an occlusion is detected.

An infusion pump system can comprise a display 20 for rendering a scannable graphical code, such as a one-dimensional or two-dimensional code, for example a bar code or a matrix code.

The display 20 may be integrated within the infusion pump.

The infusion pump may include a graphical code generator for generating a scannable graphical code based on input information.

The input information can be selected from a group consisting of: configuration data, device data, system state data, device history data, infusion history data, device alarm data and/or malfunction data.

The graphical code data generated by the code generator can be a static data or can be a serial communication data with a sequence of separate data units, such as a sequence of separate graphical data or can be a parallel communication data providing in parallel graphical code data on specified fields of the display device 20 optionally using a clock signal.

A method for displaying a graphical code on a display 20 of an infusion system comprises the steps: obtaining data from an electronic device inside the infusion pump; transforming this data into a graphical code; and displaying this graphical code on a display 20 of the infusion pump.

The step of displaying can be a static display, for example the display of a single graphical code for a predetermined amount of time or until a specific event, such as pressing a button 10 of the infusion pump.

Alternatively, the step of displaying includes the display of a sequence of graphical codes including separate individual graphical codes. This sequence can be displayed using a predefined clock signal to display each of a series of graphical displays in sequence, wherein each graphical code is displayed for a predetermined amount of time. Alternatively, the sequence can be triggered by an external event, such as by pressing a button 10 on the infusion pump, so that a user can for example flip through the code sequence.

What is claimed is:

1. An infusion device for infusion of a fluid from a reservoir into a body, the infusion device being connectable to an infusion set adaptor, the infusion device comprising:
   a drive mechanism for operatively coupling with at least a portion of the reservoir;
   a housing comprising two or more compartments, at least one being configured to contain at least a portion of the reservoir and another configured to at least partially or fully contain the drive mechanism;
   a sealing device configured to permit passage of air into and out of a first compartment of or within the housing and to inhibit passage of liquids through the sealing device between the first compartment and a neighboring compartment of or within the housing;
   a connecting site for operatively coupling the infusion set adaptor;

wherein the sealing device is arranged at a location between the first compartment and the neighboring compartment and such location is part of a path for movement of air between compartments of or within the housing whereby such movement equalizes pressure between such compartments.

2. The device according to claim 1, wherein the sealing device is arranged inside the housing between a compartment containing at least a portion of the reservoir and a compartment at least partially or fully containing the drive mechanism.

3. The device according to claim 2, wherein the sealing device is arranged between an inner area of the infusion device and a carpule compartment or a reservoir area of the infusion device.

4. The device according to claim 3, wherein the inner area comprises the drive mechanism or an enclosed compartment partially or fully containing the drive mechanism.

5. The device according to claim 1, wherein the housing does not contain a vent port.

6. The device according to claim 1, wherein the sealing device comprises at least one of a hydrophobic material, a lipophobic material, or an oleophobic material.

7. The device according to claim 1, wherein at least a portion of the sealing device is formed from one or more of a polytetrafluoroethylene polymer, a high-density polyethylene polymer, a polyethersulfon polymer, a ultra-high-molecular-weight polyethylene polymer, a polyurethane foam or a porous plastic.

8. The device according to claim 1, wherein the sealing device is joined to its location by one or more of an adhesive bond, a form fit, sonic welding, heat welding or molding.

9. The device according to claim 1, wherein the sealing device is part of an internal path that allows air pressure within the housing to equalize with air pressure outside of the housing.

10. The device according to claim 1, wherein the sealing device is formed as at least one of a seal ring, a gasket ring or an O-ring.

11. The device according to claim 1, wherein the drive mechanism further comprises a drive housing compartment that is part of the drive mechanism and at least a portion of the sealing device is in contact with and arranged between the drive housing compartment and a neighboring compartment of the infusion device.

12. The device according to claim 1, wherein at least a portion of the sealing device separates a carpule compartment of the infusion device from an enclosed compartment partially or fully containing the drive mechanism.

13. The device according to claim 12, further comprising a sealing element arranged on an inner wall of the carpule compartment and configured to be in contact with a housing of the infusion set adaptor when connected to the infusion device.

14. The device according to claim 1, wherein the sealing device comprises two or more sealing elements or sealing rings.

15. A method of equalizing pressure in an infusion device for infusion of a fluid from a reservoir into a body, the infusion device being connectable to an infusion set adaptor at a connecting site, the infusion device comprising a drive mechanism to operatively couple with at least a portion of the reservoir and a compartment sized to contain at least a portion of the drive mechanism and a carpule compartment for the reservoir, the method comprising:

providing a seal in a path from one compartment of an interior of the housing to another neighboring compartment of the interior of the housing, arranged at a location between such compartments, wherein the seal permits passage of air between the one and the neighboring compartments and inhibits passage of liquids between them, thereby equalizing air pressure in the interior of the housing and said path includes a further seal allowing equalizing with air pressure at the exterior of the housing.

16. The method of claim 15 wherein the step of providing a seal in a path from one compartment of an interior of the housing to another neighboring compartment of the interior of the housing, arranged at a location between such compartments, comprises providing at least one of a seal ring, a gasket ring or an O-ring placed between a carpule compartment and a device compartment partially or fully containing the drive mechanism.

17. The method of claim 16 wherein the step of providing a seal comprises joining a sealing device to its location by one or more of an adhesive bond, a form fit, sonic welding, heat welding or molding.

18. An infusion device for infusion of a fluid from a reservoir into a body, the infusion device being connectable to an infusion set adaptor, the infusion device comprising:
    a drive mechanism for operatively coupling with at least a portion of the reservoir;
    a housing configured to contain at least a portion of the reservoir and to at least partially or fully contain the drive mechanism;
    a sealing device configured to permit passage of air into and out of a first compartment of or within the housing and to inhibit passage of liquids through the sealing device between the first compartment and a neighboring compartment of or within the housing;
    a connecting site for operatively coupling the infusion set adaptor;
    wherein the sealing device is arranged at a location on a path for movement of air between two neighboring compartments, the two being selected from the group comprising:
    a compartment partially or fully containing the drive mechanism, a battery compartment, a carpule compartment, or a compartment containing electronic control circuitry a function key or a display.

* * * * *